United States Patent
Roche et al.

(10) Patent No.: US 11,751,922 B2
(45) Date of Patent: Sep. 12, 2023

(54) PLATFORM FRACTURE FIXATION IMPLANTS

(71) Applicant: Exactech, Inc., Gainesville, FL (US)

(72) Inventors: Christopher P. Roche, Gainesville, FL (US); David Koogle, Trenton, FL (US); Kenneth A. Egol, Rye Brook, NY (US); George S. Athwal, London (CA); Joaquin Sanchez-Sotelo, Rochester, MN (US)

(73) Assignee: Exactech, Inc., Gainesville, FL (US)

( * ) Notice: Subject to any disclaimer, the term of this patent is extended or adjusted under 35 U.S.C. 154(b) by 0 days.

(21) Appl. No.: 16/491,784

(22) PCT Filed: Mar. 12, 2018

(86) PCT No.: PCT/US2018/022042
§ 371 (c)(1),
(2) Date: Sep. 6, 2019

(87) PCT Pub. No.: WO2018/165665
PCT Pub. Date: Sep. 13, 2018

(65) Prior Publication Data
US 2021/0128205 A1 May 6, 2021

Related U.S. Application Data

(60) Provisional application No. 62/469,803, filed on Mar. 10, 2017.

(51) Int. Cl.
*A61B 17/72* (2006.01)

(52) U.S. Cl.
CPC ...... *A61B 17/7241* (2013.01); *A61B 17/7283* (2013.01)

(58) Field of Classification Search
CPC . A61B 17/72; A61B 17/7241; A61B 17/7283; A61B 17/7225; A61B 17/7233; A61B 17/7216
See application file for complete search history.

(56) References Cited

U.S. PATENT DOCUMENTS

| 2,536,964 A | 1/1951 | Stephens |
| 4,697,585 A | 10/1987 | Williams |

(Continued)

FOREIGN PATENT DOCUMENTS

| DE | 29504111 U1 | 5/1995 |
| JP | 2011519658 A | 7/2011 |

(Continued)

OTHER PUBLICATIONS

International Search Report and Written Opinion from International Application No. PCT/US2018/022042 dated May 29, 2018.

*Primary Examiner* — Eduardo C Robert
*Assistant Examiner* — Michelle C Eckman
(74) *Attorney, Agent, or Firm* — GREENBERG TRAURIG, LLP

(57) ABSTRACT

A proximal portion of an implant for repairing a multipart fracture of a proximal humerus includes an asymmetric body having a proximal end, a distal end, a medial side, a lateral side, an anterior edge, and a posterior edge a medial surface extending along at least a portion of the medial side and having a proximal end and a distal end; a protrusion forming the lateral side of the asymmetric body, offset in an anterior direction, and pointing toward a bicipital groove of the humerus when the proximal portion is implanted in the humerus, an anterior support surface configured to support a lesser tuberosity; a posterior support surface configured to support a greater tuberosity; an angled surface having a first side defined by the medial surface, a second side defined by the anterior support surface, and a third side defined by the posterior support surface; and an anchoring point.

13 Claims, 18 Drawing Sheets

(56) References Cited

U.S. PATENT DOCUMENTS

| | | | |
|---|---|---|---|
| 4,805,607 A | | 2/1989 | Englehardt et al. |
| 4,858,602 A | | 8/1989 | Seidel et al. |
| 5,509,933 A | * | 4/1996 | Davidson ............... A61B 17/72 606/280 |
| 6,077,264 A | * | 6/2000 | Chemello .......... A61B 17/7266 606/62 |
| 6,270,499 B1 | * | 8/2001 | Leu ........................ A61B 17/72 606/62 |
| 6,398,812 B1 | * | 6/2002 | Masini .................. A61F 2/4059 623/19.11 |
| 2005/0177241 A1 | * | 8/2005 | Angibaud ............. A61F 2/4014 623/19.14 |
| 2016/0166393 A1 | * | 6/2016 | Visser .................... A61B 17/72 623/19.14 |
| 2017/0151061 A1 | * | 6/2017 | Lavi ...................... A61F 2/4225 |
| 2017/0265915 A1 | * | 9/2017 | Langdale ............. A61B 17/725 |
| 2018/0199967 A1 | * | 7/2018 | Russo .................. A61F 2/4014 |

FOREIGN PATENT DOCUMENTS

| | | | | |
|---|---|---|---|---|
| WO | 2003/065913 A1 | | 8/2003 | |
| WO | WO-2014058314 A1 | * | 4/2014 | ............. A61B 17/72 |
| WO | WO-2018165665 A1 | * | 9/2018 | ............. A61B 17/74 |

* cited by examiner

PLATFORM FRACTURE FIXATION IMPLANTS

RELATED APPLICATIONS

This application is a national phase filing under 35 USC 371 of International Application No. PCT/US2018/022042, filed on Mar. 12, 2018, which claims the benefit of U.S. Provisional Patent Application No. 62/469,803, filed Mar. 10, 2017, the contents of which are incorporated by reference herein in their entirety.

FIELD OF THE INVENTION

The field of invention relates to implants for repair of long bone fractures.

BACKGROUND OF THE INVENTION

Open reconstruction of long bone fractures presents multiple challenges for the orthopedic surgeon and traumatologist, impacting their ability to reliably treat the traumatic injury. Specifically, variations in patient anatomy, fracture patterns, patient health quality, and patient co-morbidities all influence the quality of fracture reconstruction and also impact the rate and probability of fracture healing over time. As a result of these numerous variables, multiple implant options have been devised for open reduction and internal fixation of long bone fractures, including: intramedullary nails, locking plates, wires, and screws (all of which are provided in kits of numerous sizes and materials). Each implant type is associated with its own features & benefits and also its inherent complication rates for its intended use in different fracture patterns and bones.

Despite geographic and ethnic uniformity of the types of bone fractures, there exists no clear consensus of treatment method as it relates to implant type. The selection of a particular implant for a given fracture type varies and depends on multiple factors including implant design features, scope, instrumentation, and inherent mechanical integrity provided by the device for a particular fracture type and bone quality.

BRIEF DESCRIPTION OF THE FIGURES

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

SUMMARY OF THE INVENTION

Figure 1:
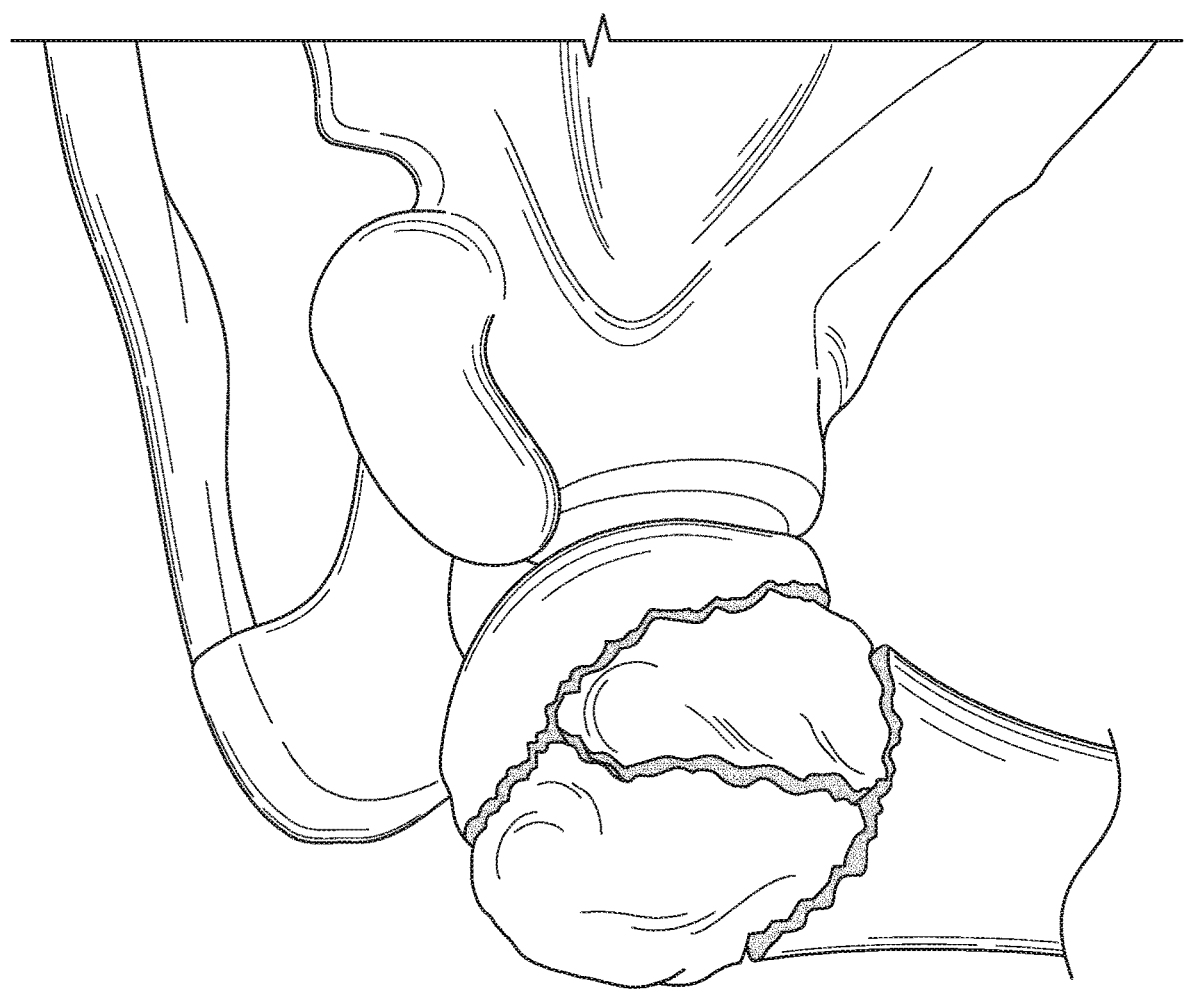
FIG. 1 shows fracture lines in a four-part fracture of the proximal humerus.

The exemplary embodiments relate to a trauma system that provides numerous different fracture reconstruction solutions.

In an embodiment, a proximal portion of an implant for repairing a multipart fracture of a proximal end of a humerus of a human is provided, the proximal portion including an asymmetric body having a proximal end, a distal end opposite the proximal end, a medial side, a lateral side opposite the medial side, an anterior edge, and a posterior edge opposite the anterior edge; a medial surface extending along at least a portion of the medial side, the medial surface having a proximal end and a distal end; a protrusion forming the lateral side of the asymmetric body, the protrusion being offset in an anterior direction, the protrusion extending in a direction so as to point toward a bicipital groove of the humerus when the proximal portion is implanted in the humerus, an anterior support surface defined by an anterior side of the protrusion and extending to the anterior edge of the asymmetric body, the anterior support surface being configured to support a lesser tuberosity of the proximal end of the humerus; a posterior support surface defined by a posterior side of the protrusion and extending to the posterior edge of the asymmetric body, the posterior support surface being configured to support a greater tuberosity of the proximal end of the humerus; a generally triangular angled surface having a first side defined by the proximal end of the medial surface, a second side defined by a proximal end of the anterior support surface, and a third side defined by a proximal end of the posterior support surface; and at least one anchoring point formed in the asymmetric body, the at least one anchoring point configured to engage an anchoring device to thereby anchor the proximal portion to a portion of the humerus.

In an embodiment, the proximal portion also includes an engagement mechanism positioned at the distal end of the asymmetric body and configured to engage a distal portion of the implant. In an embodiment, the engagement mechanism is a taper. In an embodiment, the proximal portion is integrally formed with a distal portion of the implant.

In an embodiment, the protrusion includes a fin.

In an embodiment, the at least one anchoring point includes at least one threaded hole configured to receive at least one screw. In an embodiment, the proximal portion also includes a plurality of suture holes.

In an embodiment, at least a portion of an outer surface of the proximal portion is porous.

In an embodiment, the proximal portion also includes a humeral head support engagement point configured to engage a humeral head support. In an embodiment, the angled surface forms the engagement point. In an embodiment, at least one of the anterior support surface and the posterior support surface is concave.

In an embodiment, a kit for repairing a multipart fracture of a proximal end of a humerus of a human includes a plurality of proximal portions, each of the plurality of proximal portions including: an asymmetric body having a proximal end, a distal end opposite the proximal end, a medial side, a lateral side opposite the medial side, an anterior edge, and a posterior edge opposite the anterior edge; a medial surface extending along at least a portion of the medial side, the medial surface having a proximal end and a distal end; a protrusion forming the lateral side of the asymmetric body, the protrusion being offset in an anterior direction, the protrusion extending in a direction so as to point toward a bicipital groove of the humerus when the proximal portion is implanted in the humerus, an anterior support surface defined by an anterior side of the protrusion and extending to the anterior edge of the asymmetric body, the anterior support surface being configured to support a lesser tuberosity of the proximal end of the humerus; a posterior support surface defined by a posterior side of the protrusion and extending to the posterior edge of the asymmetric body, the posterior support surface being configured to support a greater tuberosity of the proximal end of the humerus; a generally triangular angled surface having a first side defined by the proximal end of the medial surface, a second side defined by a proximal end of the anterior support surface, and a third side defined by a proximal end of the posterior support surface; at least one anchoring point formed in the asymmetric body, the at least one anchoring point configured to engage an anchoring device to thereby anchor the proximal portion to a portion of the humerus; and an engagement mechanism positioned at the distal end of the asymmetric body and configured to engage a distal portion of the implant, wherein each of the proximal portions within the kit is differently sized from all others of the proximal portions within the kit; the kit also including a plurality of distal portions, each of the distal portions having a distal end configured for placement within a medullary cavity of the humerus and a proximal end configured for engagement with the engagement mechanism of a selected one of the plurality of proximal portions, wherein each of the plurality of distal portions within the kit is differently sized from all others of the proximal portions within the kit; and the kit also including at least one humeral head support configured for attachment to the selected one of the plurality of proximal portions, each of the at least one humeral head support including a medial surface, a lateral surface opposite the medial surface of the humeral head support, a proximal end, a distal end opposite the distal end of the humeral head support, and at least one anchoring point configured to engage an anchoring device, wherein the proximal end of each of the at least one humeral head support has a profile that is complementary to the angled surface of the selected one of the proximal portions lateral surface of the humeral head support is positioned adjacent the surface of the proximal portion of the implant, and wherein the lateral surface of the humeral head support is configured to support a humeral head of the humerus during a repair of a four-part fracture of the humerus.

In an embodiment, each of the plurality of proximal portions has a different size in a proximal-distal direction. In an embodiment, each of the plurality of proximal portions has a different size in an anterior-posterior direction. In an embodiment, each of the plurality of distal portions has a different length or a different diameter from all of the other distal portions within the kit.

In an embodiment, the engagement mechanism of the plurality of proximal portions includes a taper. In an embodiment, the at least one anchoring point of each of the proximal portions includes at least one threaded hole configured to receive at least one screw. In an embodiment, at least one of the anterior support surface and the posterior support surface of at least one of the proximal portions is concave.

In an embodiment, a humeral head support for use in an implant for repairing a multipart fracture of a proximal end of a humerus of a human is provided, the humeral head support including a base portion configured for attachment to a proximal end of the implant; and a support portion configured to support a humeral head of the humerus during a repair of a four-part fracture of the humerus.

In an embodiment, the humeral head support has a medial surface, a lateral surface opposite the medial surface of the humeral head support, a proximal end, a distal end opposite the distal end of the humeral head support, and at least one anchoring point configured to engage an anchoring device, and the base portion configured for attachment to the proximal end of the implant includes the proximal end of the humeral head support having a profile that is complementary to a surface of the proximal portion of the implant when the lateral surface of the humeral head support is positioned adjacent the surface of the proximal portion of the implant.

In an embodiment, the humeral head support also includes at least one anchoring point. In an embodiment, the at least one anchoring point includes at least one threaded hole configured to receive at least one screw.

DETAILED DESCRIPTION OF THE INVENTION

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "in one embodiment," "in an embodiment," and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

The exemplary embodiments relate to platform fracture fixation implants (alternately referred to herein as "implants" for brevity) and kits including such implants, which facilitate reconstruction of long bone fractures using multiple different sizes and methods of treatment, in a simpler and more inventory efficient manner. The exemplary embodiments may be suitable for cost sensitive yet anatomically diverse markets served by multiple orthopedic surgeons who may have been trained using various techniques, as the exemplary embodiments can provide many different sizes and options for implant fixation methods. In some embodiments, exemplary implants and kits including exemplary implants may be suitable to address reconstructing fractures of long bones, and more specifically of the humerus. More particularly, the exemplary embodiments illustrated in the accompanying drawings are shown in use reconstructing the proximal humeral head and/or midshaft of the humerus. In other embodiments, implants may be suitable to address reconstructing fractures of other long bones, such as the proximal and distal segments of the femur and tibia, fibula, radius, ulna, clavicle, etc.

When an orthopedic surgeon or traumatologist attempts to reconstruct a one- or two-part fracture of the proximal humerus, the shoulder joint may be incised with as small an opening as possible in order to protect the rotator cuff and other surrounding musculature from any further damage. However, when an orthopedic surgeon or traumatologist attempts to reconstruct a three- or four-part fracture of the proximal humerus, the shoulder joint may to be opened in order to adequately reconstruct all the bone fragments. Consequently, a surgeon may attempt to reconstruct these different classifications of proximal humeral fractures by different methods. In some embodiments, a platform fracture fixation implant is modular so that it can be pre-assembled on the "back table" as a single unit of appropriate size for a particular patient anatomy or fracture pattern (i.e., so that it can be configured as an intramedullary rod which can be inserted through a small incision for a one- or two-part fracture), or can be assembled in situ by positioning a distal portion with the fracture line (or aligned at the level of the surgical humeral neck) and then positioning a proximal portion, which is shaped to be a scaffold by which it can be used to reconstruct multiple boney fragments (as in a three- or four-part fracture) around the proximal portion. FIG. 1 shows the fracture lines of a four-part fracture of the proximal humerus, with a first fracture line extending horizontally along the surgical neck, a second fracture line extending superiorly through the bicipital groove, and a third fracture line extending along the plane of the humeral head at the level of the anatomic neck of the humerus. A four-part fracture is termed as such because these three fracture lines create four parts: (1) the humeral head, (2) the lesser tuberosity, (3) the greater tuberosity, and (4) the humeral shaft.

Figure 2:
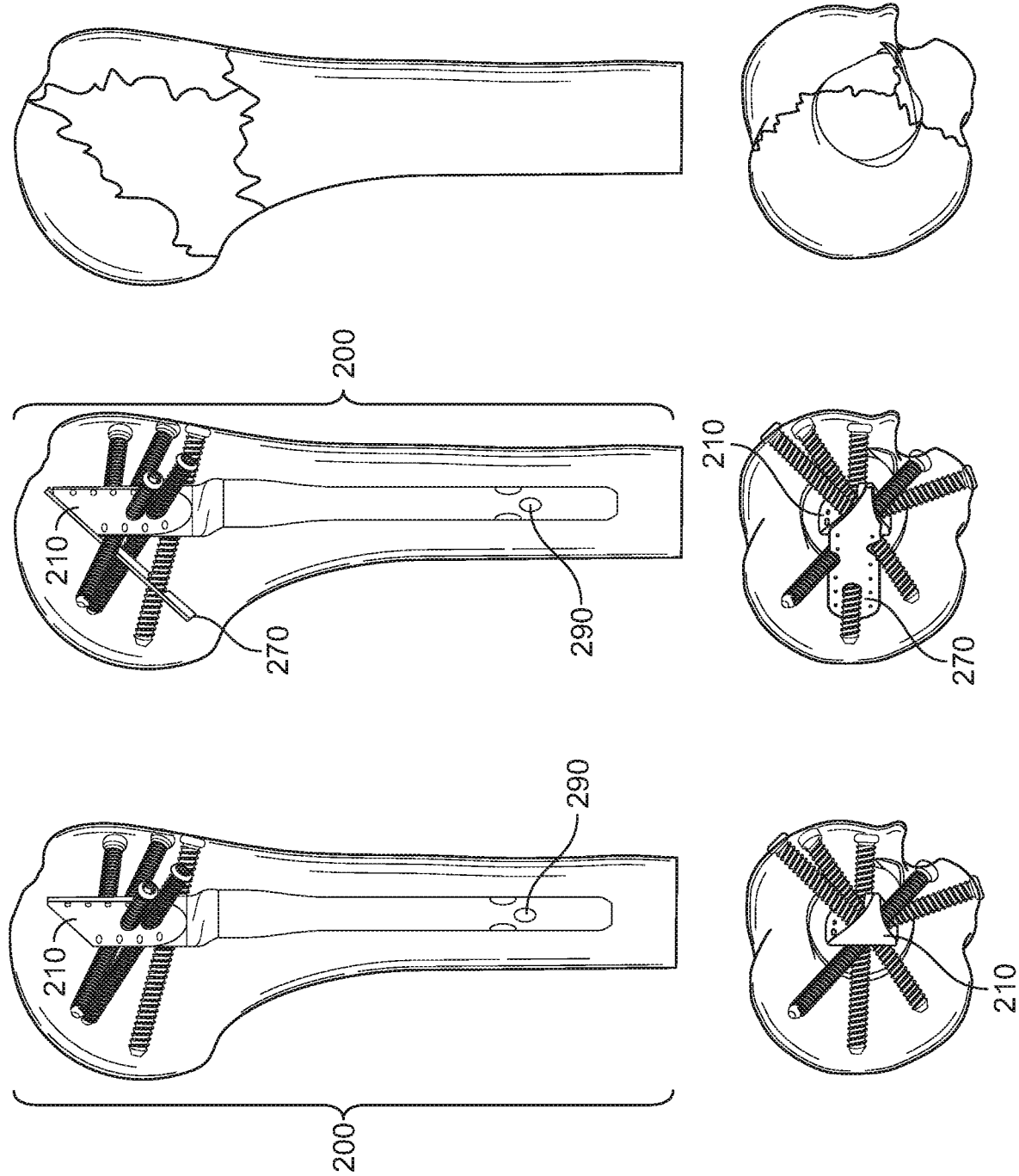
FIG. 2 shows a first embodiment of a platform fracture fixation implant including a first embodiment of a proximal portion of a platform fracture fixation implant, with fracture lines in a four-part fracture of the proximal humerus shown for reference.

In some embodiments, a platform/scaffold is used to affix or co-opt the bone fragments as is traditionally done with hemiarthroplasty, and is used in conjunction with a modular nail. In some embodiments, a proximal portion is noncylindrical and asymmetric in design so that it is provided in left and right sides to respect the different shapes and sizes of the lesser and greater tuberosities of the proximal humerus. Referring now to FIGS. 2-6, a first embodiment of a platform fracture fixation implant 200 (for brevity, "implant 200") is shown. FIG. 2 shows the first embodiment of a platform fracture fixation implant 200 from side and top perspectives, with a four-part fracture of the proximal end of a humerus shown for reference in the top right and bottom right.

In an embodiment, the implant 200 includes an asymmetric proximal portion 210 for improved tuberosity reconstruction. In some embodiments, the asymmetric proximal portion 210 includes at least one anchoring point 262 (e.g., a threaded hole) configured to receive screws or other anchoring elements, thereby to anchor portions of the humerus to the asymmetric proximal portion 210. In an embodiment, as shown in the top left and bottom left of FIG. 2, the implant 200 does not include a humeral head support. In an embodiment, as shown in the top center and bottom center of FIG. 2, the implant includes a humeral head support 270. In some embodiments, the modular humeral head support 270 can be attached to the proximal portion 210 to provide additional humeral head support.

In some embodiments, additional humeral head support can help to avoid varus collapse in the clinical scenario where the medial calcar is involved/disrupted by the trauma. In some embodiments, screws or other anchoring devices can be secured through or directly to the humeral head support 270 to act as a buttress and strengthen the construct. In an embodiment, the proximal portion 210 provides a smaller space for the lesser tuberosity and a larger space for the greater tuberosity. In an embodiment, a protrusion 240 (e.g., a fin) is oriented toward the bicipital groove to aid the surgeon in reconstructing the fractured components in the patient's native humeral head retroversion.

In some embodiments, the implant 200 includes a distal portion 290 that is generally cylindrical. In some embodiments, the distal portion 290 is configured as a hollow intramedullary nail (see FIG. 4). In some embodiments, the distal portion 290 is configured as a modular (e.g., cemented or press fit) humeral stem. In some embodiments, the distal portion 290 includes supplemental fixation features along the length of the implant. In some embodiments, the distal portion 290 does not include supplemental fixation features along the length of the implant.

Figure 3:
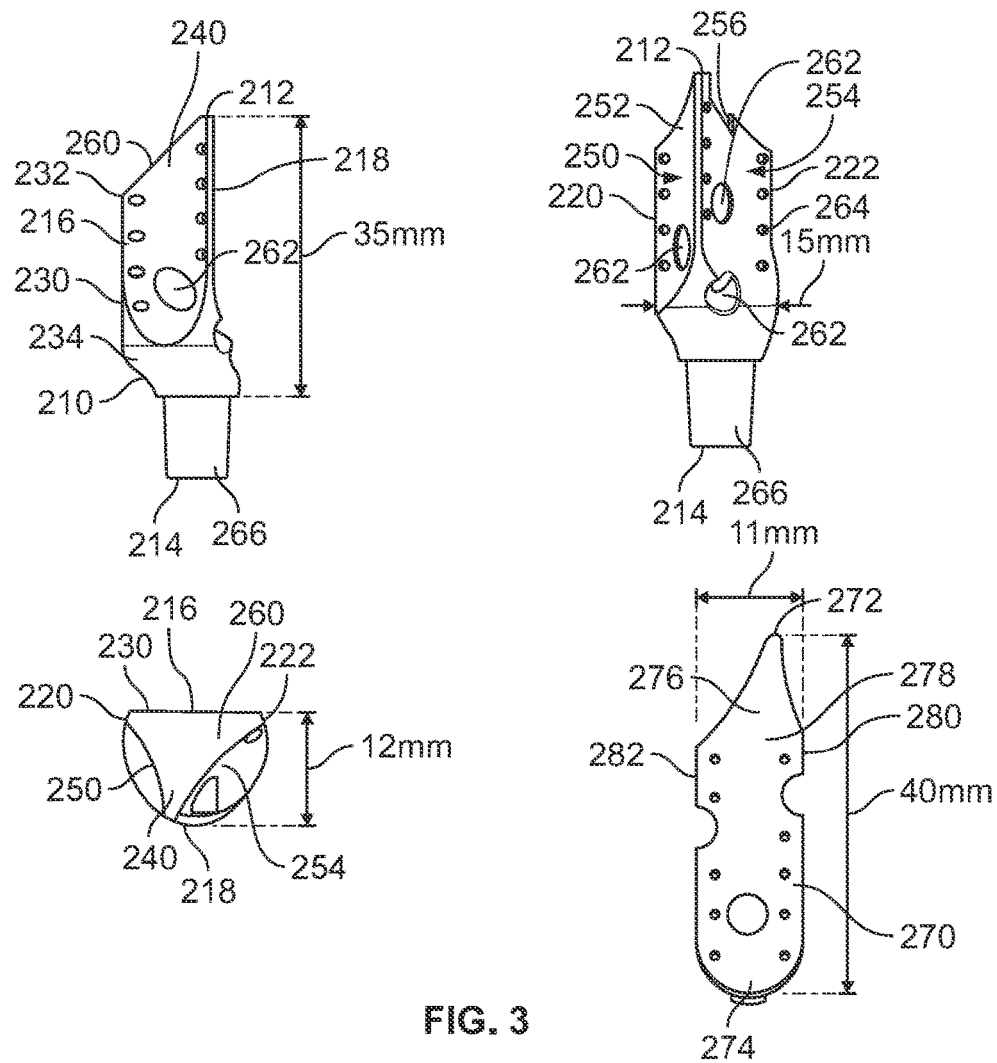
FIG. 3 shows a detailed view of the proximal portion of FIG. 2.

FIG. 3 shows a detailed view of a first embodiment of a proximal portion 210 of an implant that is used in the implant 200 of FIG. 2. FIG. 3 includes dimensional measurements for various portions of the proximal portion 210 shown therein, but it will be apparent to those of skill in the art that these are only exemplary dimensions and that the proximal portion 210 of FIG. 3 may be provided in various sizes. In some embodiments, the proximal portion 210 includes a proximal end 212, a distal end 214, a medial side 216, a lateral side 218, an anterior edge 220, and a posterior edge 222. In some embodiments, the proximal portion 210 includes a medial surface 230 having a proximal end 232 and a distal end 234.

In an embodiment, a proximal portion 210 includes an asymmetric body to facilitate tuberosity reconstruction. In an embodiment, an anterior support surface 250 is provided for the lesser tuberosity, posterior support surface 254 is provided for the greater tuberosity, and the protrusion 240 separates the anterior support surface 250 from the posterior support surface 254. In some embodiments, the anterior support surface 250 has a proximal end 252 and the posterior support surface 254 has a proximal end 256. In such an embodiment, a proximal end 210 is therefore provided in left and right sides (with a left side proximal end 210 shown in FIGS. 2, 3, 5, and 6. In an embodiment, suture holes 264 are included to aid in the bone reattachment. In an embodiment, the asymmetric proximal portion 210 is provided in multiple heights to better support the tuberosity sizes for patients of larger or smaller stature or bone size. In an embodiment, the height of the proximal portion 210 is 35 mm. In an embodiment, the height of the proximal portion 210 is in a range of from 20 to 50 mm. In an embodiment, the asymmetric proximal portion 210 is provided in multiple widths. In an embodiment, the width of the proximal portion 210 is 15 mm. In an embodiment, the width of the proximal portion 210 is in a range of from 10 mm to 40 mm. In an embodiment, the asymmetric proximal portion 210 is provided in multiple thicknesses. In an embodiment, the thickness of the proximal portion 210 is 12 mm. In an embodiment, the thickness of the proximal portion 210 is in a range of from 5 mm to 50 mm. In an embodiment, the radii, positions, and orientations of the protrusion 240 may be differently configured in any of the aforementioned size ranges. In some embodiments, the radii, positions, and orientations of the protrusion 240 may be configured to accommodate a lesser tuberosity that is generally 50% to 80% of the size of the greater tuberosity, and such that the protrusion 240 points to the bicipital groove. In some embodiments, a kit may include various embodiments of the asymmetric proximal portion 210 having heights, widths, and depths of varying proportions with respect to one another in order to provide for the anatomical variations of different patients. In some embodiments, a distal end 214 of the proximal portion 210 is provided with a male taper 266 (i.e., an engagement mechanism). In some embodiments, the male taper 266 has a diameter of 10 mm. In some embodiments, the male taper 266 has a diameter in a range of from 7 mm to 14 mm. In some embodiments, a size of the distal end 214 of the distal portion 210 may vary based on a size of the proximal portion 210 and/or a size of the implant 200 as a whole. In some embodiments, the distal end 214 of the proximal portion 210 may be provided with another suitable type of engagement mechanism for engaging the distal portion 290.

In an embodiment, the asymmetric proximal portion 210 may include the humeral head support device 270 (see FIG. 2, top center and bottom center). In some embodiments, the humeral head support device 270 includes a proximal end 272, a distal end 274, a medial surface 276, a lateral surface 278, an anterior side 280, and a posterior side 282. In an embodiment, the humeral head support device 270 may be provided in multiple lengths. In an embodiment, the length of the humeral head support device 270 is 40 mm. In an embodiment, the length of the humeral head support device 270 is in a range of from 10 mm to 60 mm. In an embodiment, the humeral head support device 270 is provided in multiple widths. In an embodiment, the width of the humeral head support device 270 is 11 mm. In an embodiment, the width of the humeral head support 270 is in a range of from 5 mm to 35 mm. FIG. 3 includes dimensional measurements embodiments of for various portions of various dimensions of the humeral head support device 270, but it will be apparent to those of skill in the art that these are only exemplary dimensions and that the humeral head support device 270 of FIG. 3 may be provided in various sizes or shapes and also connected to the proximal portion of a humeral nail of various sizes or shapes. For example, the humeral head support device can be adapted to connect to the proximal portion of a traditional cylindrical nail. In some embodiments, the proximal portion 210 includes a substantial triangular angled surface 260 configured to engage the humeral head support device. In some embodiments, the angled surface 260 extends from the proximal end of 232 of the medial surface 230 and is defined by the proximal end 232 of the medial surface 230, the proximal end 252 of the anterior concave surface 250, and the proximal end 256 of the posterior concave surface 254. In some embodiments, a profile of a portion of the humeral head support 270 adjacent the proximal end 272 thereof is complementary to a profile to the angled surface 260 of the proximal portion 210.

Figure 4:
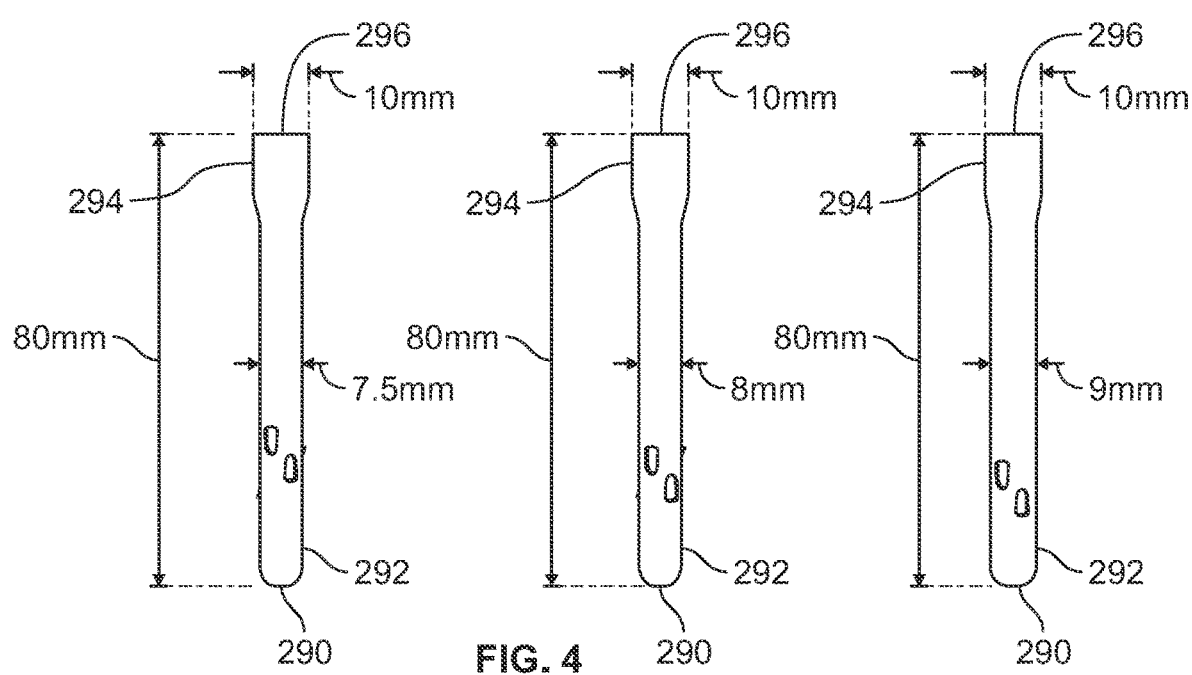
FIG. 4 shows a detailed view of embodiments of various sizes of a distal portion of the platform fracture fixation implant of FIG. 2.

FIG. 4 shows a detailed view of a first embodiment of a distal portion 290 of an implant 200 that is used in the implant 200 of FIG. 2. FIG. 4 includes dimensional measurements embodiments of for various portions of various sizes of the distal portion 290 shown therein, but it will be apparent to those of skill in the art that these are only exemplary dimensions and that the distal portion 290 of FIG. 4 may be provided in various sizes.

In some embodiments, the distal portion 290 includes locking talons 292 (i.e., supplemental fixation features) for distal fixation without the need for diaphsyeal locking screws. In some embodiments, the distal portion 290 is a stem (as with a hemiarthroplasty). In some embodiments, the distal portion 290 is a cylindrical or other-shaped (i.e., cross-sectionally shaped) shaft (as with an intramedullary nail). In some embodiments, a diameter of the distal portion 290 is a range of from 7.5 mm to 9 mm. In some embodiments, a diameter of the distal portion 290 is a range of from 7.5 mm to 20 mm. In some embodiments, a length of the distal portion 290 is 80 mm. In some embodiments, a length of the distal portion 290 is in a range of from 40 mm to 260 mm. In some embodiments, a proximal end 294 of the distal portion 290 is provided with a female taper 296 that is configured to engage the male taper 266 of the proximal portion 210. In some embodiments, the female taper 296 has a diameter of 10 mm. In some embodiments, the female taper 296 has a diameter in a range of from 7 mm to 14 mm. In some embodiments, a size of the proximal end 294 of the distal portion 290 may vary based on a size of the distal portion 290 and/or a size of the implant 200 as a whole. In some embodiments, the proximal end 294 of the distal portion 290 may be provided with another suitable type of engagement mechanism for engaging the proximal portion 210.

Figure 5:
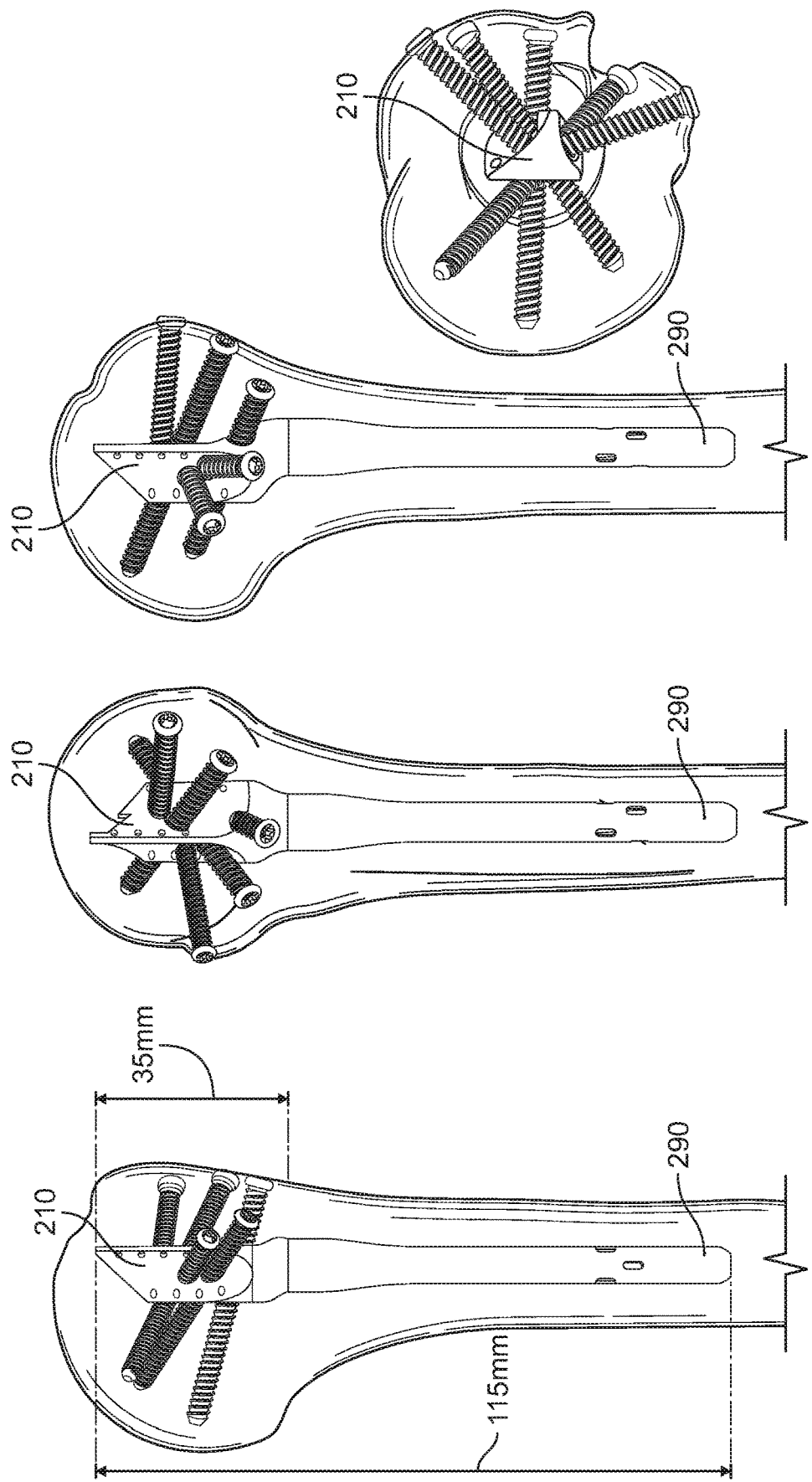
FIG. 5 shows further views of the platform fracture fixation implant of FIG. 2.

FIG. 5 shows additional views of the implant of FIG. 2. FIG. 5 includes dimensional measurements for various portions of the implant shown therein, but it will be apparent to those of skill in the art that these are only exemplary dimensions and that the implant of FIG. 5 may be provided in various sizes. In some embodiments, an implant includes an asymmetric proximal portion for improved tuberosity reconstruction.

Figure 6:
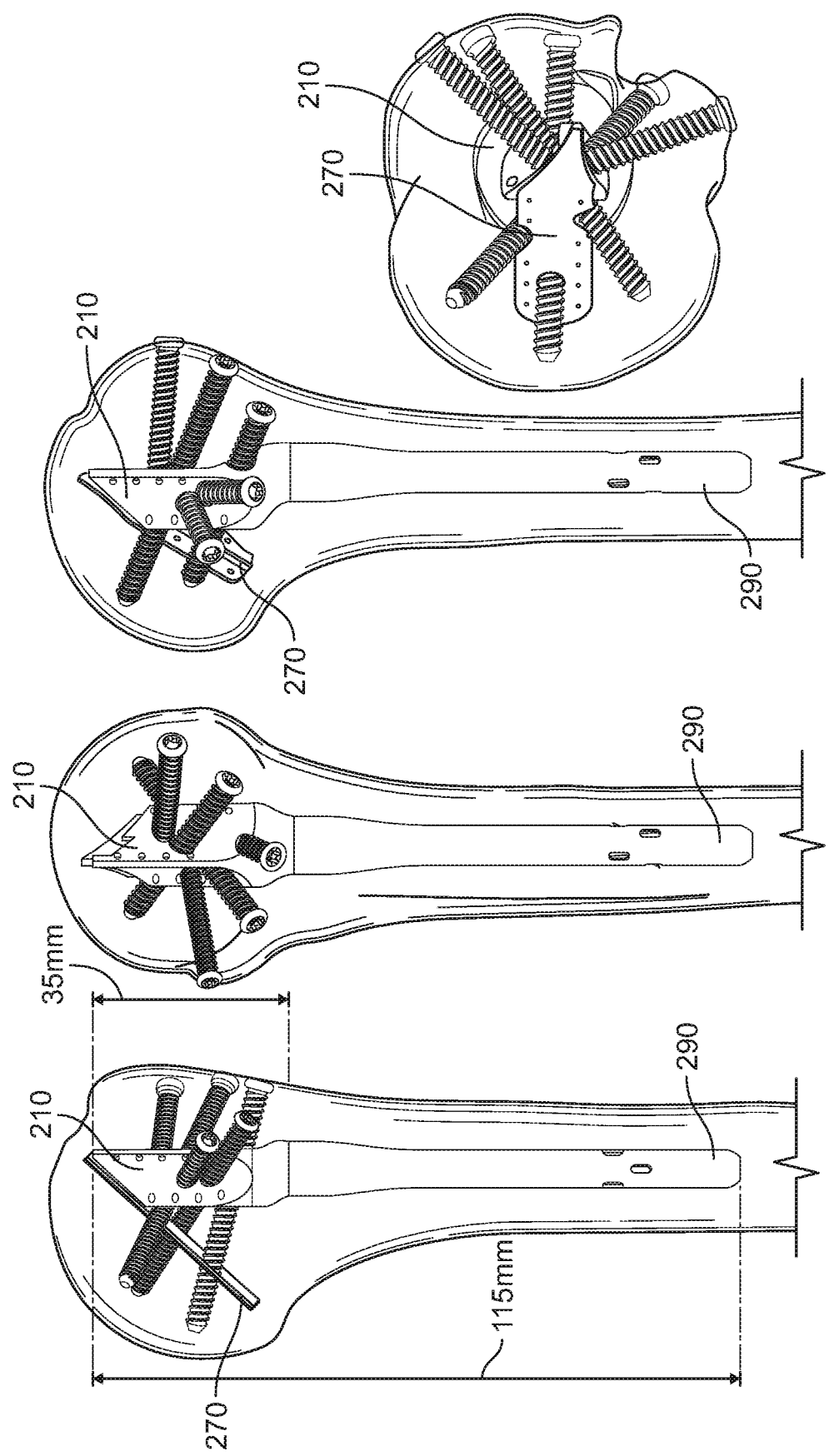
FIG. 6 shows further views of the platform fracture fixation implant of FIG. 2 in conjunction with a supplemental humeral head support.

In some embodiments, as shown in FIG. 5, an implant 200 does not include a supplemental humeral head support 270. FIG. 6 shows additional views of the implant 200 of FIG. 2. FIG. 6 includes dimensional measurements for various portions of the implant 200 shown therein, but it will be apparent to those of skill in the art that these are only exemplary dimensions and that the implant 200 of FIG. 6 may be provided in various sizes. In some embodiments, an implant 200 includes an asymmetric proximal portion for improved tuberosity reconstruction. In some embodiments, as shown in FIG. 5, an implant includes a supplemental humeral head support 270.

In some embodiments, as shown in FIGS. 2-6, an implant 200 includes a proximal 210 portion providing a smaller surface/space (e.g., anterior support surface 250) for the lesser tuberosity and a larger surface/space (e.g., posterior support surface 254) for the greater tuberosity. In some embodiments, a surgeon will need to reconstruct the bone fragments in a manner that respects the patient's original anatomy. In some embodiments, to accomplish this, the surgeon will orient the humeral head fracture according to the patients humeral head retroversion. In some embodiments, to aid in such orientation when performed in situ, the protrusion 240, which separates the lesser and greater tuberosity beds, is oriented toward the bicipital groove (which is a common fracture location involved in the fracture classification and an anatomic landmark commonly utilized/referenced for reconstructions to recreate the patients anatomic humeral head retroversion).

In some embodiments, platform fracture fixation implants, proximal portions of platform fracture fixation implants, and distal portions of platform fracture fixation implants can be provided in different lengths, widths, thicknesses and at different aspect ratios in order to best fill the proximal humeral defect and function as a scaffold to reconstruct the components around. It will be known to those of skill in the art that the proximal humerus anatomy is highly variable. Therefore, in some embodiments, implants are provided in different sizes such that the proximal portions thereof are provided in a patient-size specific manner, which would thereby better configure the position of the screws for the patient's fracture.

Figure 7:
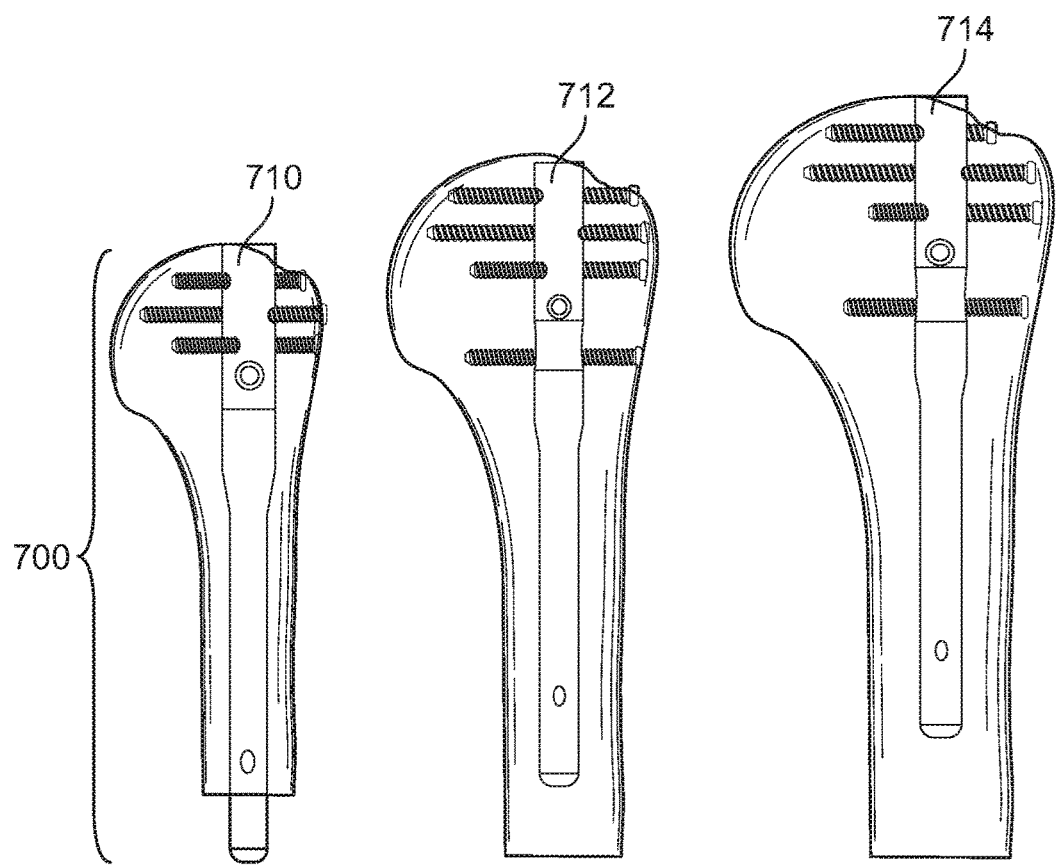
FIG. 7 shows embodiments of various sizes of a second embodiment of a platform fracture fixation implant including a second embodiment of a proximal portion of a platform fracture fixation implant.
Figure 8:
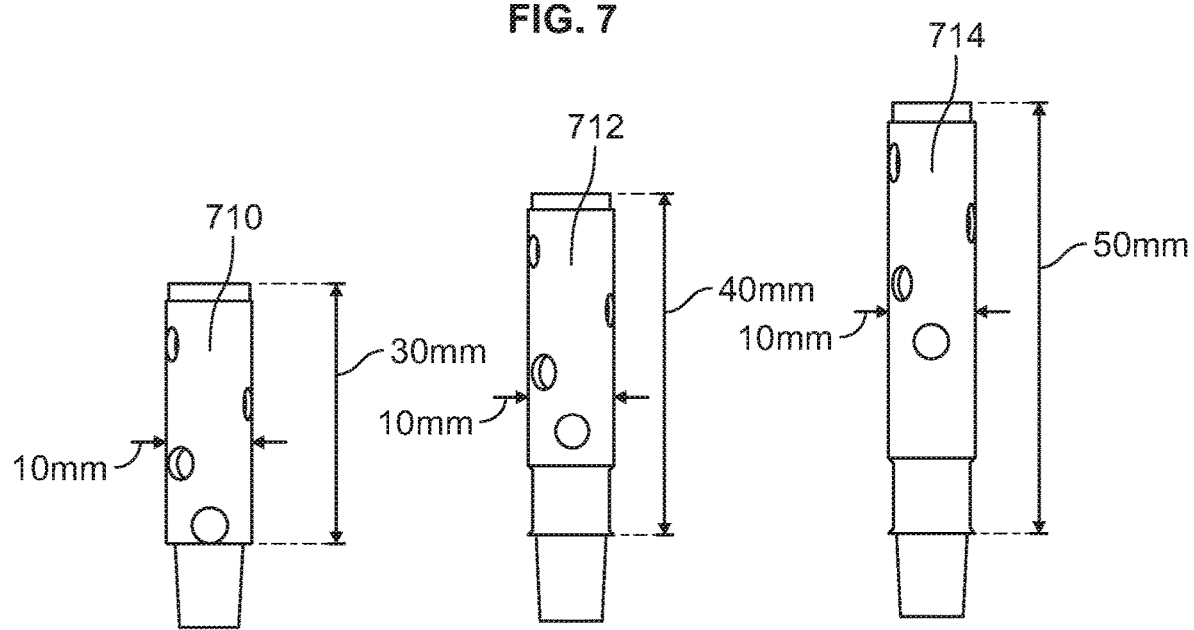
FIG. 8 shows a detailed view of embodiments of various sizes of the proximal portion of FIG. 7.

In some embodiments, a modular platform fracture fixation implant kit may include may include differing embodiments of proximal portions and/or distal portions. FIG. 7 shows a second embodiment of a platform fracture fixation implant 700. In the embodiment of FIG. 7, an implant 700 includes an intramedullary nail that utilizes multiple locking screws in differently-sized proximal segments 710, 712, 714 to ensure anatomically-correct screw positions through the bone fragments for various sizes of humeral anatomies. In some embodiments, the intramedullary nail of FIG. 7 may also be adapted to accept the humeral head support piece 270 depicted in FIGS. 2, 3, and 6. FIG. 8 shows embodiments of various sizes of a second embodiment of a proximal portion that may form the proximal portion of the implant of FIG. 7 (e.g., a small size 710, a medium size 712, and a large size 714). FIG. 8 includes dimensional measurements for various portions of the variously sized embodiments of the proximal portion shown therein, but it will be apparent to those of skill in the art that these are only exemplary dimensions and that the proximal portion of FIG. 8 may be provided in various sizes. In some embodiments, the implant 700 of FIG. 7 including the proximal portion of FIG. 8 facilitates in situ reconstruction of proximal humeral fractures and provides for improved tuberosity reconstruction, while accounting for various humeral head sizes and anatomic variations.

Figure 9:
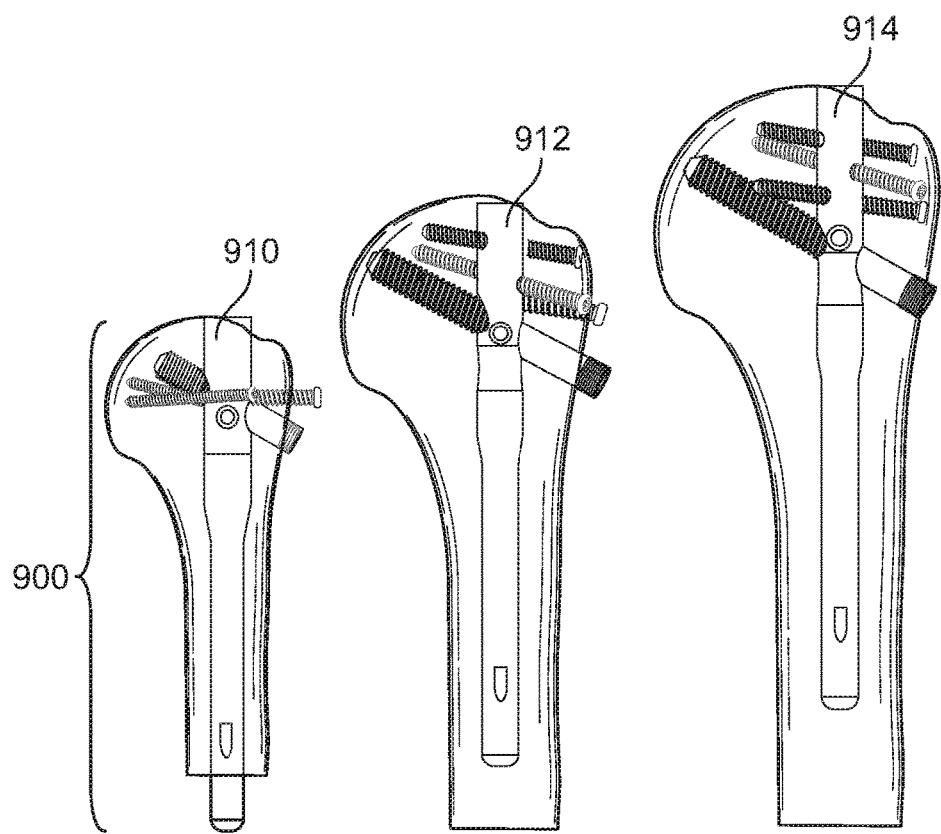
FIG. 9 shows embodiments of various sizes of a third embodiment of a platform fracture fixation implant including a third embodiment of a proximal portion of a platform fracture fixation implant.
Figure 10:
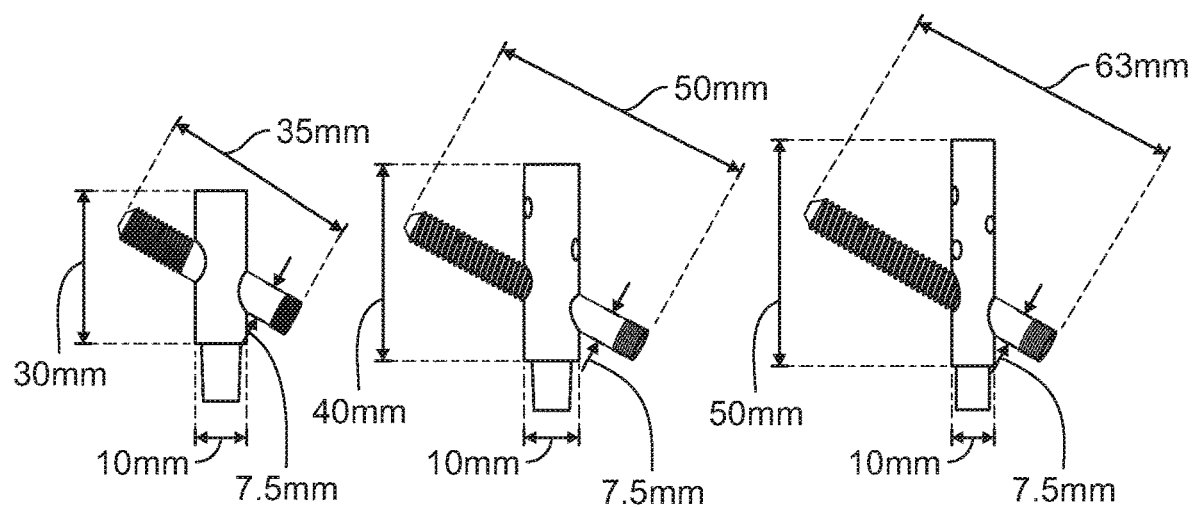
FIG. 10 shows a detailed view of embodiments of various sizes of the proximal portion of FIG. 9.

In some embodiments, a cephlalomedullary style of proximal portion is utilized in multiple sizes in order to position a larger lag screw in the center of the humeral head (or some other desired location), despite significant anatomic variation in humeral head size, humeral head diameter, and humeral head medial/lateral and anterior/posterior offset relative to the intramedullary canal. FIG. 9 shows a third embodiment of a platform fracture fixation implant 900 including a cephlalomedullary style of proximal portion 910, 912, 914. More particularly, FIG. 9 shows multiple views of a third embodiment of platform fracture fixation implant, showing multiple sizes of a proximal portion (e.g., a small size 910, a medium size 912, a large size 914) of a straight nail with a lag screw to facilitate insertion of the lag screw in the center of the humeral head (accounting for various humeral head sizes) when reconstructing proximal humeral fractures. FIG. 10 shows embodiments of various sizes of a third embodiment of a proximal portion 910, 912, 914 that may form the proximal portion of the implant 900 of FIG. 9. FIG. 10 includes dimensional measurements for various portions of the variously sized embodiments of the proximal portion shown therein, but it will be apparent to those of skill in the art that these are only exemplary dimensions and that the proximal portion of FIG. 10 may be provided in various sizes. In some embodiments, the proximal portions of FIG. 10 provide various sizes of an implant 900 that is a straight nail with a lag screw, to facilitate insertion of the lag screw in the center of the humeral head (accounting for various humeral head sizes) when reconstructing proximal humeral fractures.

Figure 11:
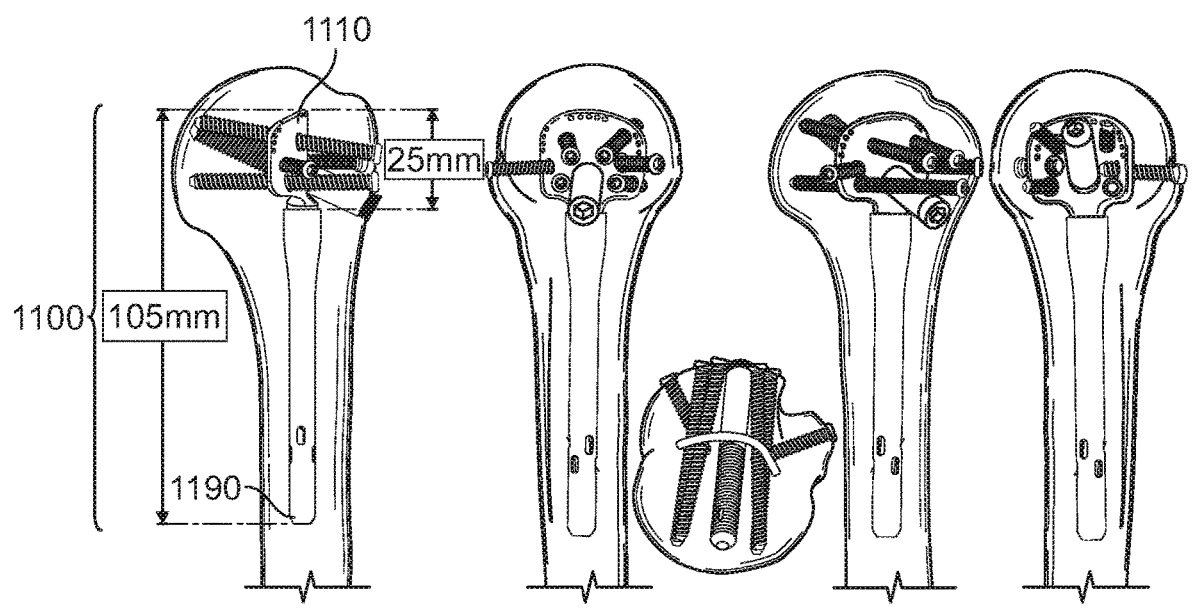
FIG. 11 shows various views of a fourth embodiment of a platform fracture fixation implant including a fourth embodiment of a proximal portion of a platform fracture fixation implant.
Figure 12:
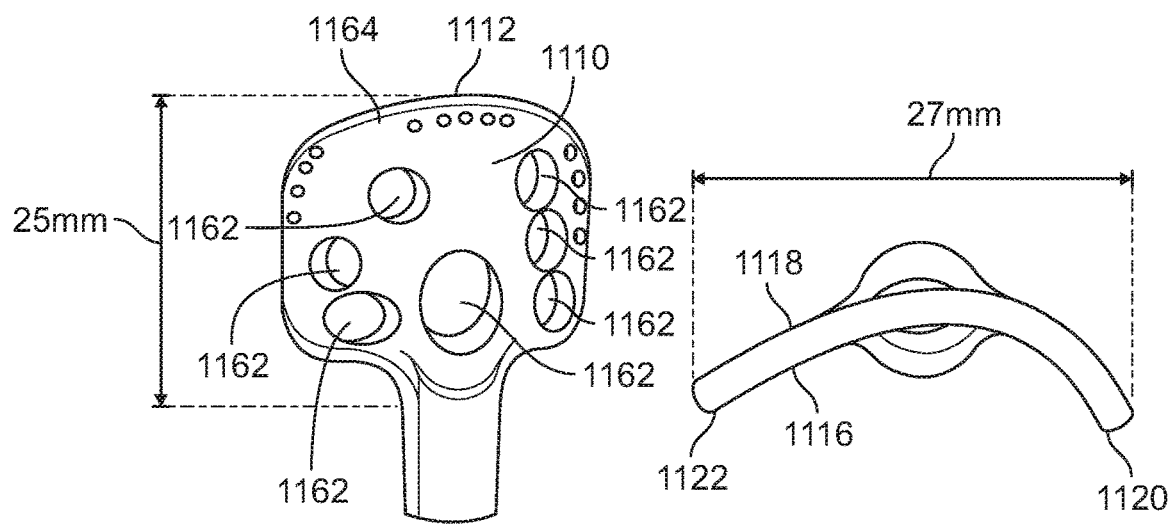
FIG. 12 shows a detailed view of the proximal portion of FIG. 11.

FIG. 11 shows a fourth embodiment of a platform fracture fixation implant 1100 including a cephlalomedullary style of proximal portion 1110. More particularly, FIG. 11 shows multiple views of a third embodiment of a platform fracture fixation implant, showing multiple views of a proximal portion that is asymmetric in shape to provide a more rotationally stable reconstruction than the traditional cylinder. In the embodiment of FIG. 11, the extensions of the proximal portion in the directions of both the lesser and greater tuberosities provide for better distribution of screws within the fractured bone to prevent a stress concentration and provide more compression to the fragments. FIG. 12 shows multiple views of a fourth embodiment of a proximal portion 1110 that may form the proximal portion of the implant of FIG. 11. In some embodiments, the proximal portion 1110 includes a proximal end 1112, a distal end 1114, a medial side 1116, a lateral side 1118, an anterior end 1120, and a posterior end 1122. FIG. 12 includes dimensional measurements for various portions of the proximal portion 1110 shown therein, but it will be apparent to those of skill in the art that these are only exemplary dimensions and that the proximal portion 1110 of FIG. 12 may be provided in various sizes. As noted above, the cephlalomedullary proximal portion 1110 of FIG. 12 is asymmetric and is therefore more rotationally stable than a cylinder for improved tuberosity reconstruction.

In the embodiment of FIG. 12, the locations 1162 for attachment of the screws are distributed across the proximal portion 1110 and suture holes 1164 are provided to aid in the bone reattachment. In the embodiment of FIG. 12, a proximal portion 1110 has a height of 25 mm and a width of 27 mm. In some embodiments, a proximal portion 1110 has a height in a range of from 5 mm to 45 mm and a width in a range of from 7 mm to 47 mm. In some embodiments, varying sizes of a proximal portion 1110 may account for patients' differently-sized humeral heads, as depicted for the aforementioned cephlalomedullary design, thereby ensuring that the central lag screw is positioned in the center of the humeral head regardless of the patient's humeral head size (i.e., diameter and/or thickness) or the patient's humeral head offset (i.e., medial/lateral or anterior/posterior) relative to the intramedullary axis.

Figure 13:
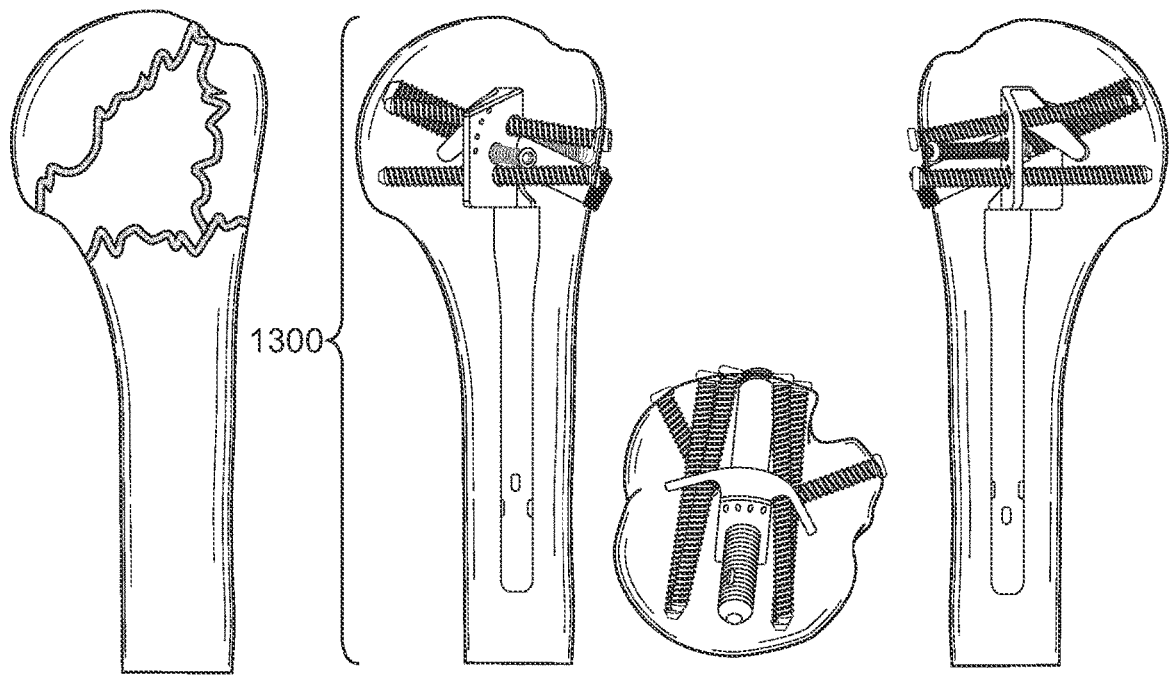
FIG. 13 shows various views of a fifth embodiment of a platform fracture fixation implant including a fifth embodiment of a proximal portion of a platform fracture fixation implant, with fracture lines in a four-part fracture of the proximal humerus shown for reference.

FIG. 13 shows a fifth embodiment of a platform fracture fixation implant 1300 including a cephalomedullary style of proximal portion 1310. More particularly, FIG. 13 shows multiple views of a third embodiment of a platform fracture fixation implant 1300, showing multiple sizes of a proximal portion 1310 that is asymmetric in shape to provide a more rotationally stable reconstruction than the traditional cylinder. In the embodiment of FIG. 13, a medial support 1370 is integrated into the proximal portion to provide improved humeral head support in the case of medial calcar disruption. Similar to the embodiment of FIGS. 11 and 12, in the embodiment of FIG. 13, locations 1362 for screw attachment are spread from the central axis in order to better distribute the screws through the fractured tuberosities into the humeral head while maintaining a large central lag screw. A four-part fracture of the proximal humerus is shown for reference to the top left.

Figure 14:
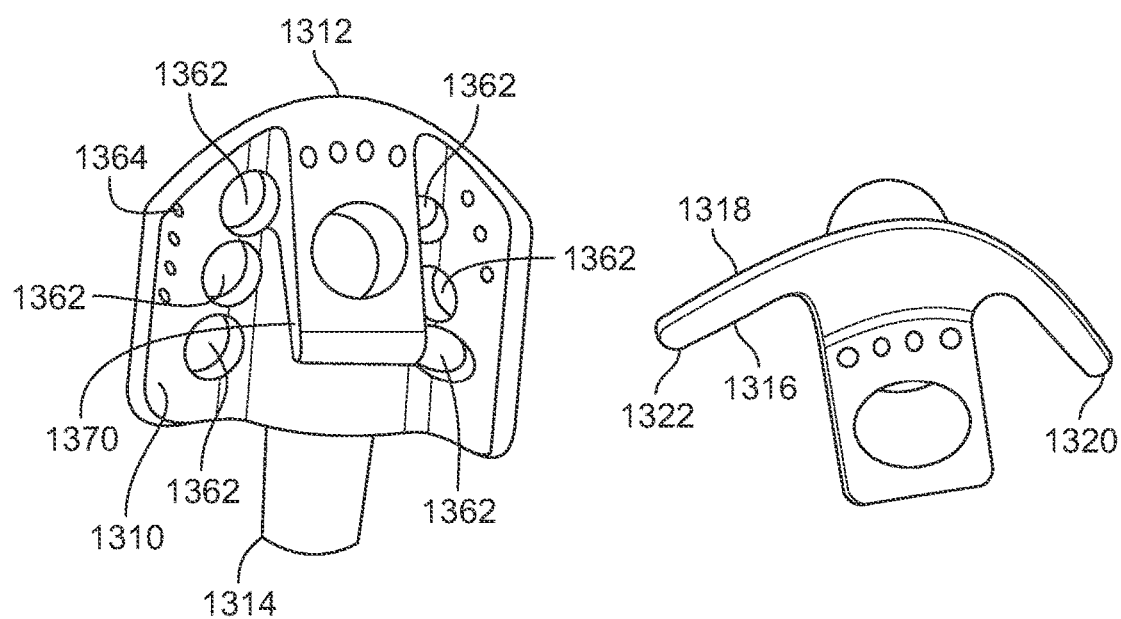
FIG. 14 shows a detailed view of the proximal portion of FIG. 13.

FIG. 14 shows multiple views of a fifth embodiment of a proximal portion 1362 that may form the proximal portion of the implant of FIG. 13. In some embodiments, the proximal portion 1310 includes a proximal end 1312, a distal end 1314, a medial side 1316, a lateral side 1318, an anterior end 1320, and a posterior end 1322. As noted above, the cephlalomedullary proximal portion of FIG. 14 is asymmetric and is therefore more rotationally stable than a cylinder for improved tuberosity reconstruction. The locations 1362 for attachment of the screws are distributed throughout the proximal portion and suture holes 1364 are provided to aid in the bone reattachment. The proximal portion 1310 of FIG. 14 includes a medial support 1370 to provide improved humeral head support in the case of medial calcar disruption.

Figure 15:
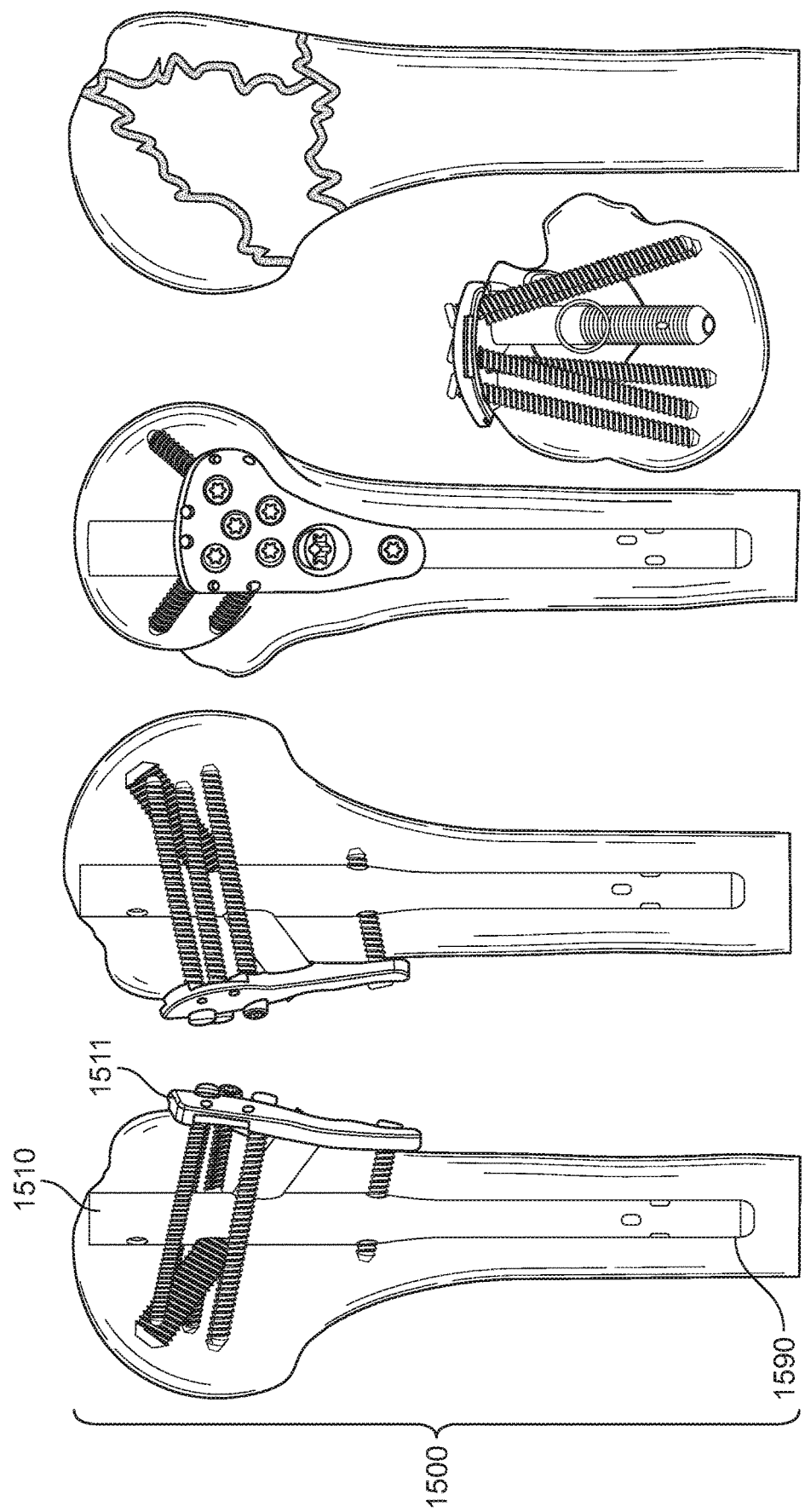
FIG. 15 shows various views of a sixth embodiment of a platform fracture fixation implant including a fifth embodiment of a proximal portion of a fracture fixation implant and a locking plate, with fracture lines in a four-part fracture of the proximal humerus shown for reference.

In some embodiments, a proximal humeral nail and a locking plate are used in conjunction with one another. Such embodiments may be suitable for use to repair severe and multipart comminuted fractures. In some embodiments of a modular platform fracture fixation implant, this combination can be accomplished by providing multiple sizes of a proximal nail portion in any of the aforementioned configurations while ensuring the central lag is centered in the humeral head, with the plate positioned ideally on the lateral humerus, and achieving a sufficient distribution of screws into the fractured bone. FIG. 15 illustrates various views of a sixth embodiment of a platform fracture fixation implant 1500 having a proximal portion 1510, which is combined with a locking plate 1511, and a distal nail portion 1590. A four-part fracture of the proximal humerus is shown on the right for reference. In the embodiment of FIG. 15, the locations for screw attachment are spread from the central axis in order to better distribute the screws through the fractured tuberosities into the humeral head while maintaining a large central lag screw and positioning the plate on the lateral proximal humerus bone for added stability in multi-part fractures. In some embodiments, the screws that attach the locking plate may also lock into the intramedullary nail for added construct stiffness.

Figure 16:
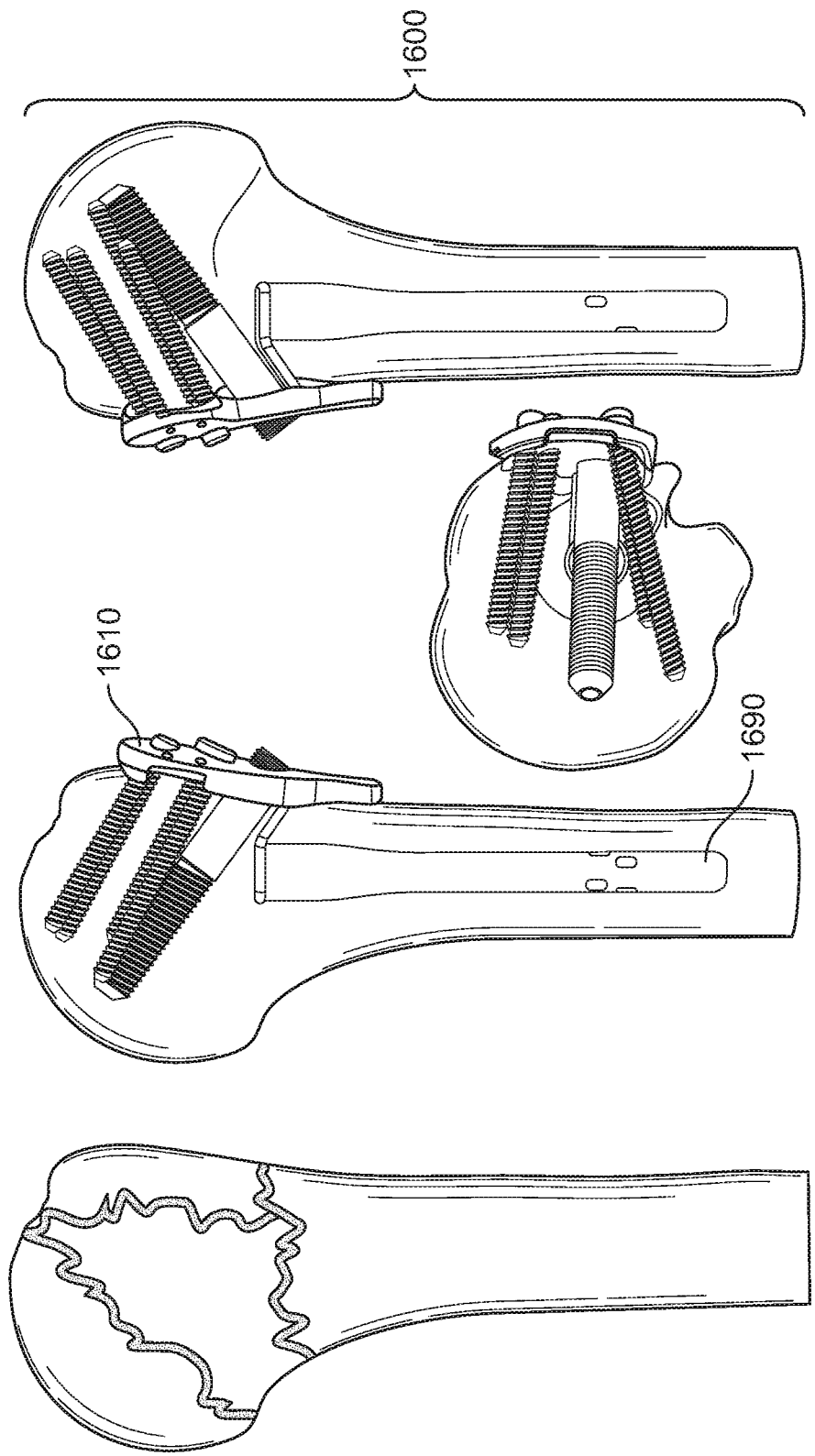
FIG. 16 shows various views of a seventh embodiment of a platform fracture fixation implant including a seventh embodiment of a proximal portion of a fracture fixation implant and an embodiment of a locking plate, with fracture lines in a four-part fracture of the proximal humerus shown for reference.

In some embodiments, the distal end of a locking plate is configured to include a modular connection to the proximal end of the distal nail, for construction of a hybrid nail plate (with or without a proximal nail component). FIG. 16 illustrates various views of a seventh embodiment of a platform fracture fixation implant 1600, which has a taper connection between a locking plate 1610 and a distal nail 1690. A four-part fracture of the proximal humerus is shown for reference on the left. In the embodiment of FIG. 16, the locations for screw attachment are spread from the central axis in order to better distribute the screws through the fractured tuberosities into the humeral head while maintaining a distal platform segment for added rotational stability and bending resistance. In the embodiment of FIG. 16, a central lag screw is included.

Figure 17:
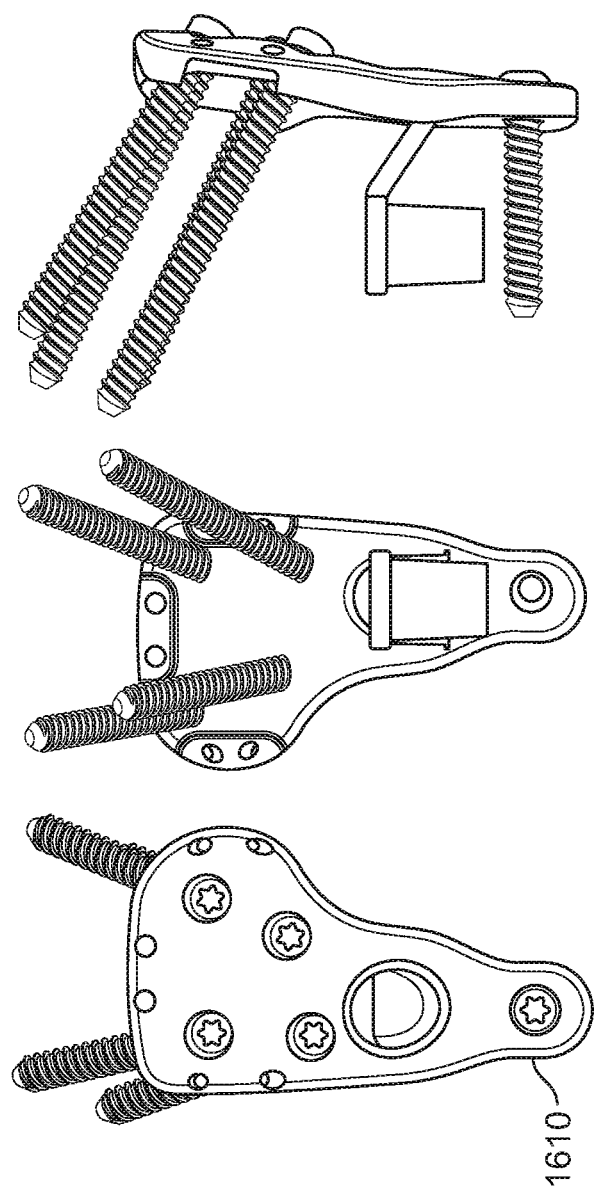
FIG. 17 shows a detailed view of the proximal portion and locking plate of FIG. 16.

FIG. 17 illustrates various views of an embodiment of a locking plate 1610 that forms a portion of the implant of FIG. 16, and may be referred to as a seventh embodiment of a proximal portion of a platform fracture fixation implant 1600. In the embodiment of FIG. 17, a lateral locking plate 1610 includes a modular connection for securing to the distal portion of platform fracture fixation implant 1600. In the embodiment of FIG. 17, a central lag screw (not shown) may be included or may be omitted. In some embodiments, a taper connection is modularly connected to the locking plate, to improve manufacturability and to enable use without the taper if so desired as a stand-alone locking plate.

Figure 18:
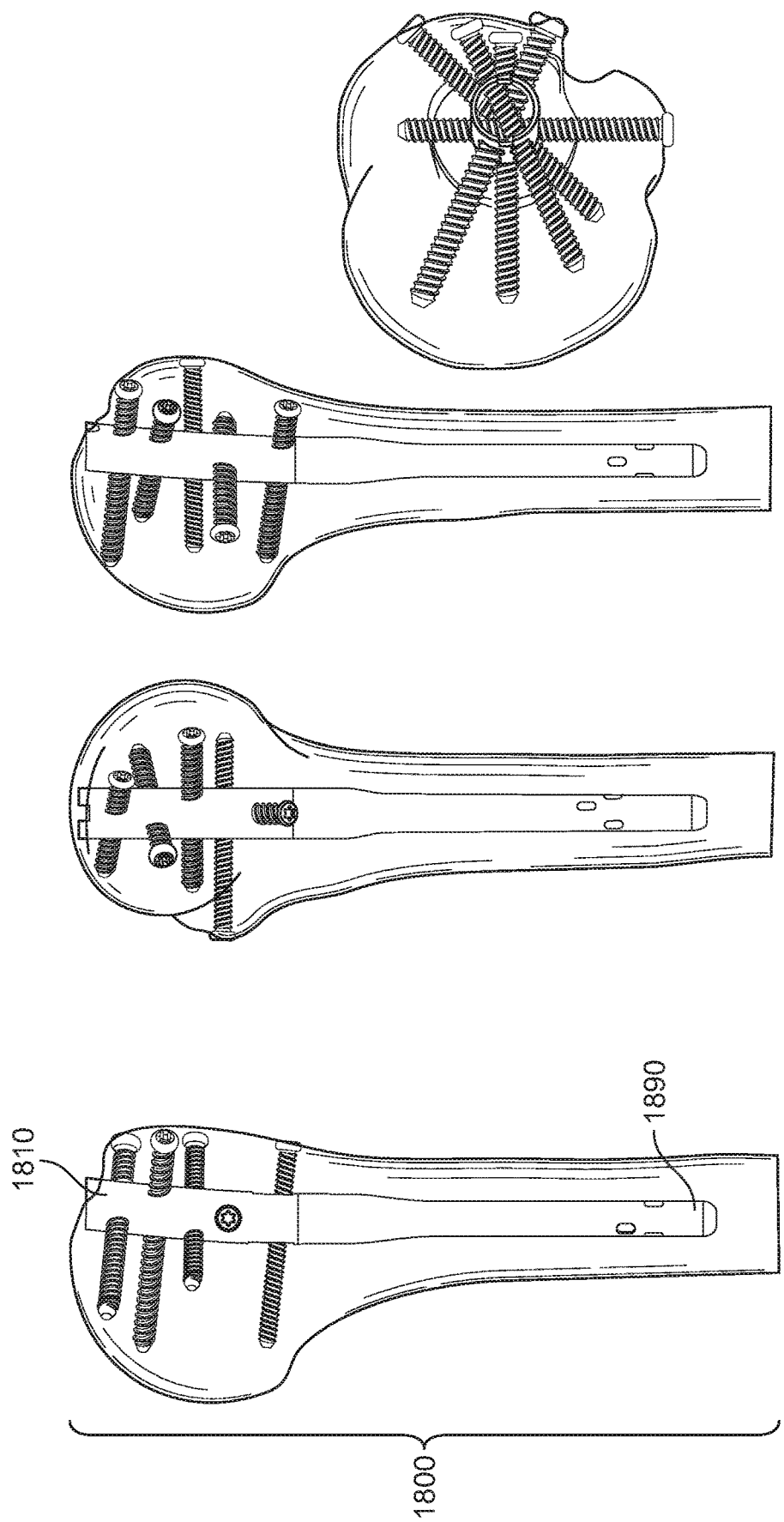
FIG. 18 shows various views of an eighth embodiment of a platform fracture fixation implant including an eighth embodiment of a proximal portion of a platform fracture fixation implant.

For mid-shaft fractures or one- or two-part fractures of the proximal humerus, surgeons may wish to insert a nail through a small incision on the superior humeral head. FIG. 18 illustrates various views of an eighth embodiment of a platform fracture fixation implant 1800, which may be suitable for such techniques, together with a distal nail portion 1890. FIG. 18 includes dimensions for various portions of the platform fracture fixation implant 1800 shown therein, but those of skill in the art will understand that these dimensions are only exemplary and that the platform fracture fixation implant of FIG. 18 may be provided in a variety of sizes. In the embodiment, of FIG. 18, a platform fracture fixation implant is in the form of a curved nail. In some embodiments, an implant is back-table pre-assembled. In some embodiments, an appropriately-sized proximal portion is selected from a kit, and has a bend adapted to facilitate insertion while minimizing damage to a patient's rotator cuff or surrounding musculature.

Figure 19:
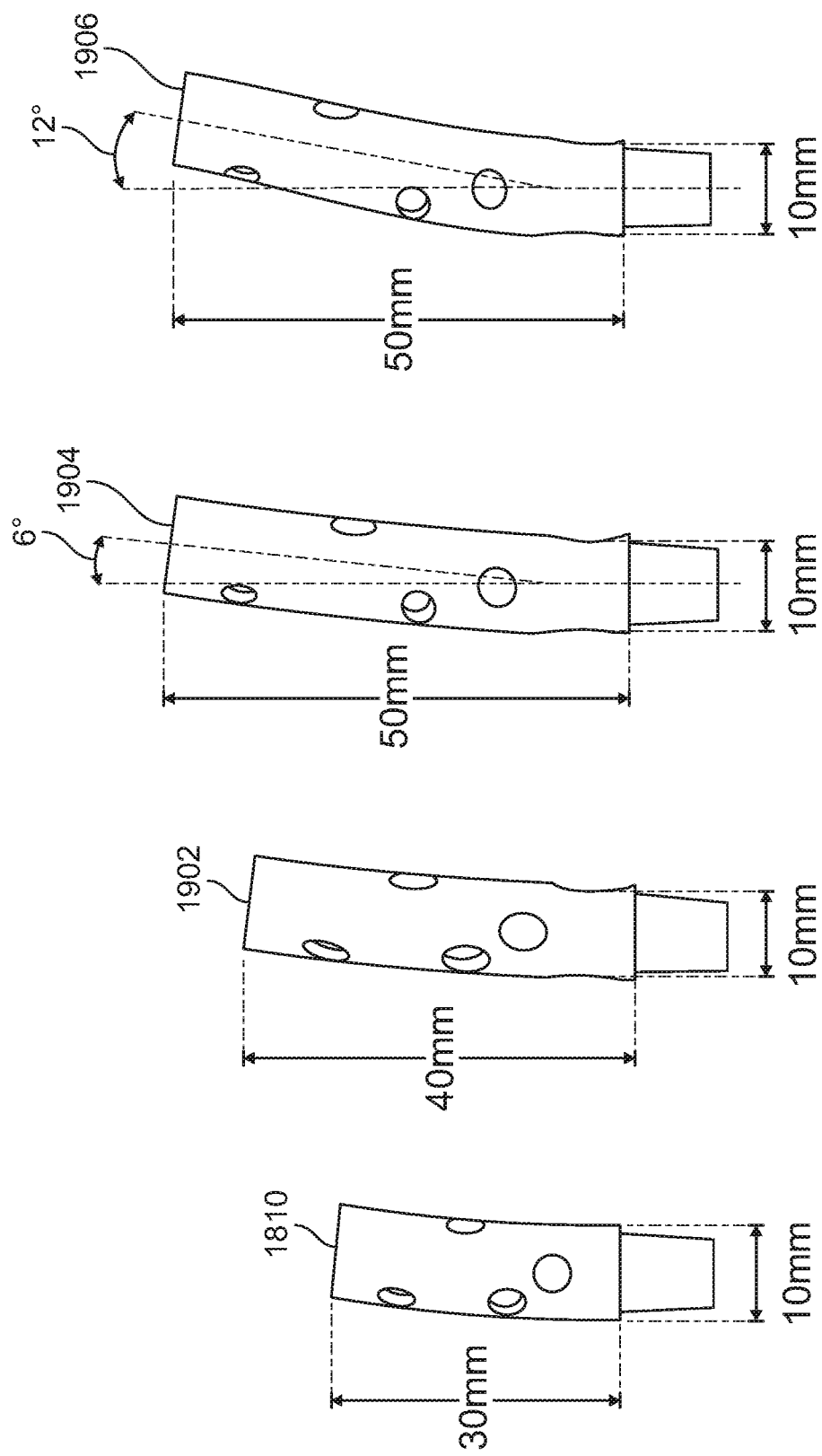
FIG. 19 shows a detailed view of embodiments of various sizes and configurations of the proximal portion of FIG. 18.

FIG. 19 shows embodiments of various sizes of an eighth embodiment of a proximal portion (e.g., a small size 1810, a medium size 1902, a large size 1904, and a high-angle large size 1906) that may form the proximal portion of the implant 1800 of FIG. 18. FIG. 19 includes dimensional measurements for various portions of the variously sized embodiments of the proximal portion shown therein, but it will be apparent to those of skill in the art that these are only exemplary dimensions and that the proximal portion of FIG.

19 may be provided in various sizes. In some embodiments, the angled bend of the proximal portion of FIG. 19 may vary to account for various humerus sizes and anatomic variations. In the embodiments shown in FIG. 19, an angled bend may vary in a range of from an angle of 6° to an angle of 12°. In some embodiments, an angled bend may vary in a range of from an angle of 0° to an angle of 20°.

Figure 20:
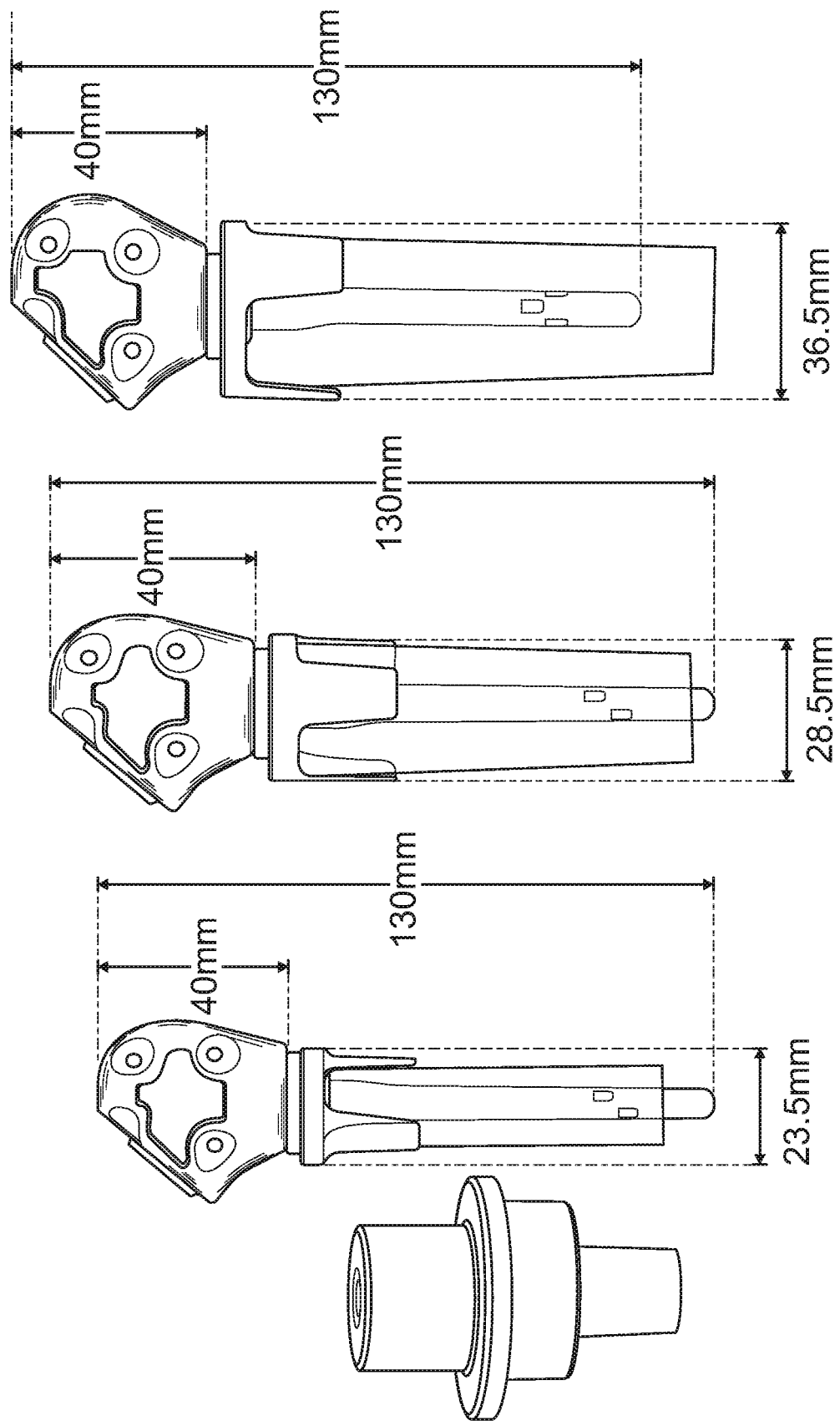
FIG. 20 shows embodiments of various sizes of a ninth embodiment of a platform fracture fixation implant including a proximal portion that is an adapter suitable for revision as an arthroplasty.

In some embodiments, a kit provides for revision scenarios. Arthroplasty is commonly used as the revision should a fracture fail to heal. FIG. 20 shows an adapter providing the ability to convert a failed fracture reconstruction to a shoulder arthroplasty 2000 (e.g., a hemi arthroplasty, a total shoulder arthroplasty, or a reverse total shoulder arthroplasty) using a taper and screw connection, or other similar connecting means. More particularly, FIG. 20 shows a modular taper adapter (adapter shown detached to the left) in a variety of sizes (e.g., a small size 2002, a medium size 2004, and a large size 2006) that may enable the conversion of a platform fracture fixation implant to a hemi arthroplasty, a total shoulder arthroplasty, or a reverse total shoulder arthroplasty, all of which could be secured to the proximal portion of the adapter of FIG. 20. In FIG. 20, an adapter is shown as connected to various sizes of a prosthesis sold under the trademark EQUINOXE by Exactech, Inc. of Gainesville, Fla.

Figure 21:
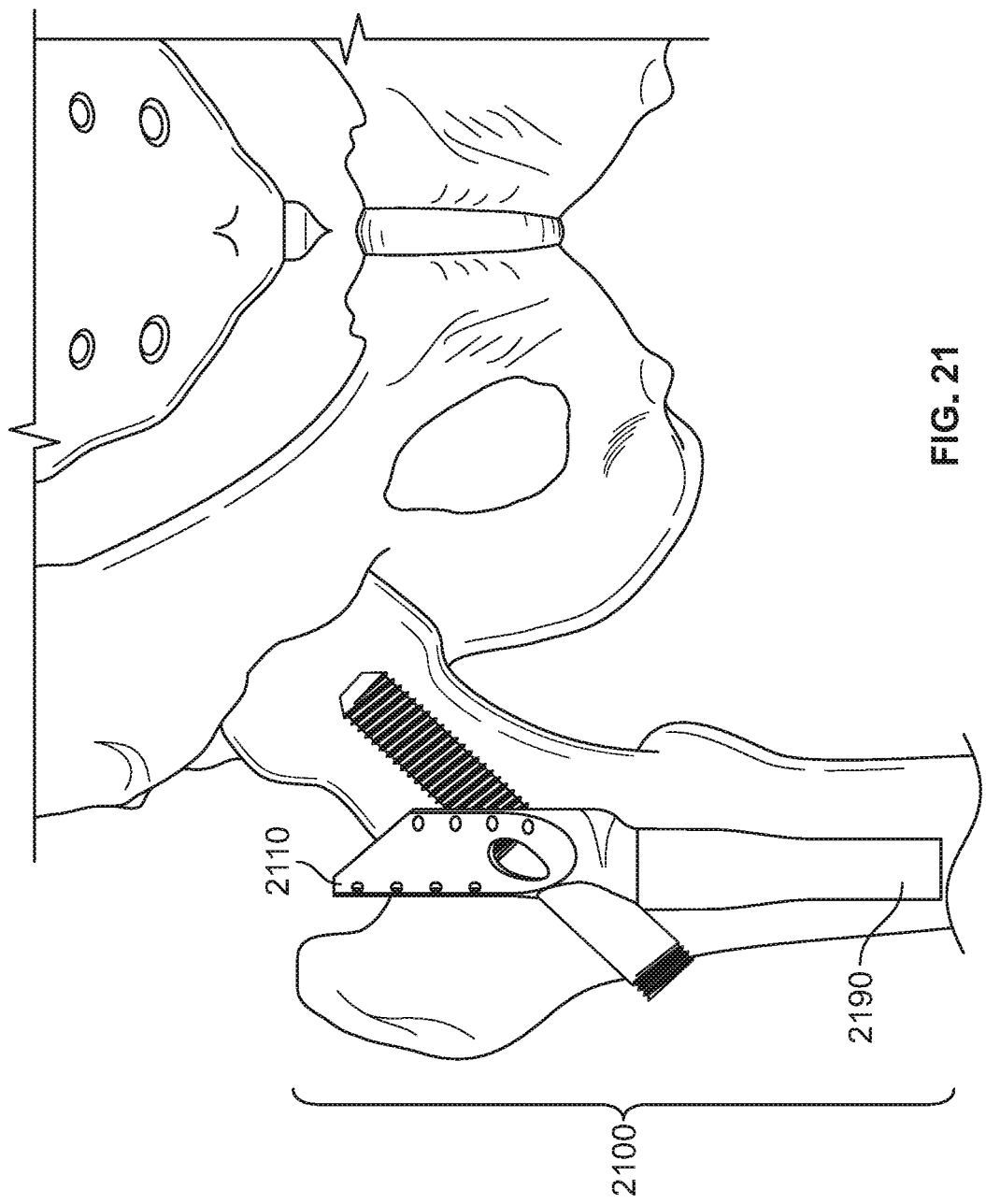
FIG. 21 shows a tenth embodiment of a platform fracture fixation implant that is configured for use to repair a femoral neck fracture.

In some embodiments, the various modular proximal and distal portions of platform fracture fixation implants described above may be provided in different shape variations than those described herein. In some embodiments, talon-like fixation units may be used to gain bony purchase of the fragments or shaft of the long bone. In some embodiments, bone screws may be used. In some embodiments, the modular segments of platform fracture fixation implants (i.e., various proximal and distal portions) may be affixed or keyed to one other by various methods including taper locking, threaded sections, or slide and cross pinned connection to allow various rotational orientations. In some embodiments, screw connections can be threaded or be slip fit, as appropriate. In some embodiments, any of the concepts embodied by the various modular proximal and distal portions of platform fracture fixation implants describe above may be applied to other long bones (e.g., the proximal and distal segments of the femur, tibia, fibula, radius, ulna, clavicle, etc.). FIG. 21 shows only one such variation, in which an implant 2100, including a proximal portion 2110 and a distal portion 2190, is adapted to be positioned in the proximal femur in order to reconstruct a femoral neck fracture.

Figure 22:
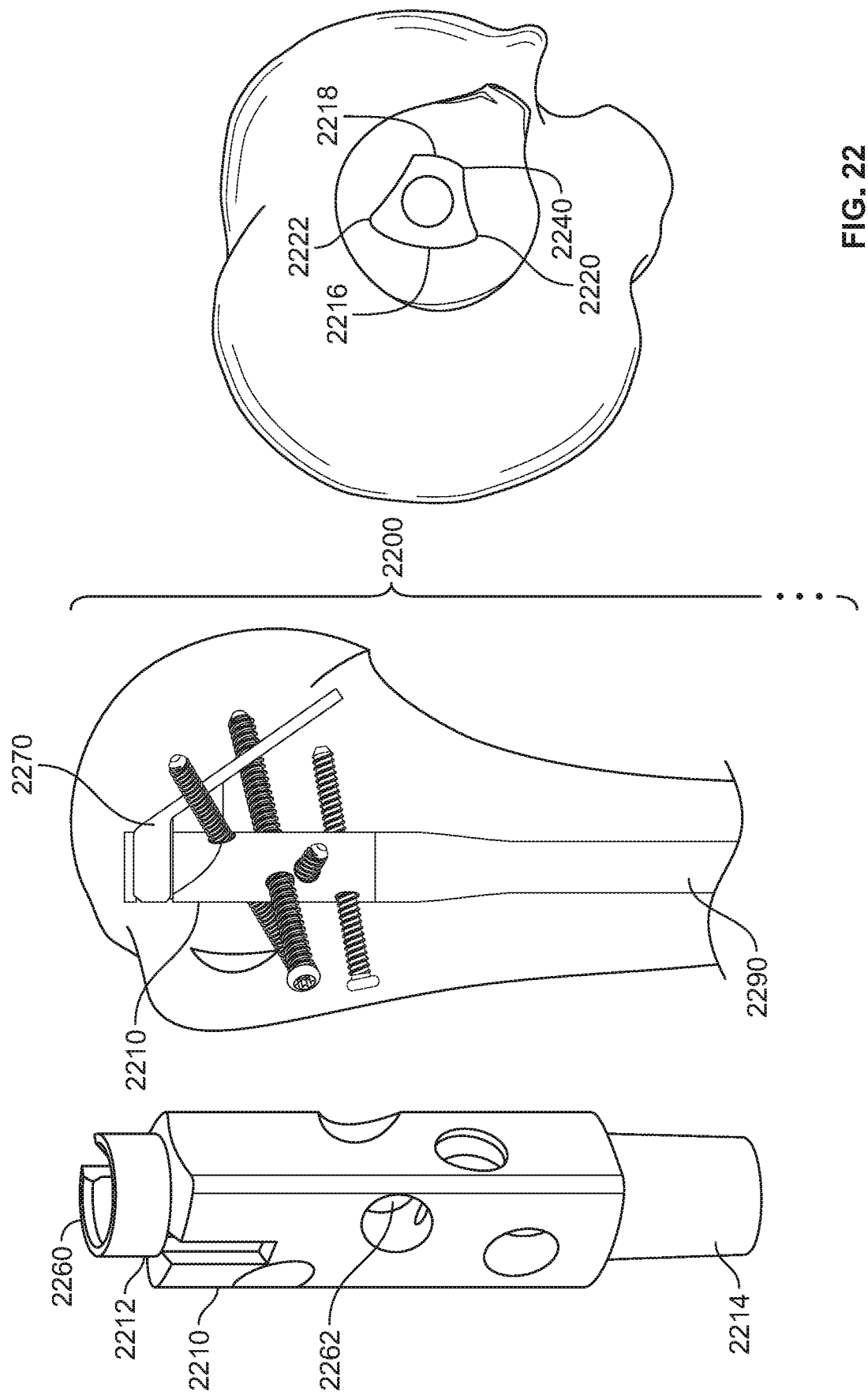
FIG. 22 shows an eleventh embodiment of a platform fracture fixation implant including an eleventh embodiment of a proximal portion of a platform fracture fixation implant and a humeral head support.

FIG. 22 illustrates various views of a eleventh exemplary embodiment of a platform fracture fixation implant 2200. In some embodiments, the platform fracture fixation implant 2200 includes a proximal portion 2210 and a distal portion 2290. In some embodiments, the proximal portion 2210 includes at least one anchoring point 2262 (e.g., a threaded hole) configured to receive screws or other anchoring elements, thereby to anchor portions of the humerus to the asymmetric proximal portion 2210. In some embodiments, the proximal portion 2210 includes a protrusion 2240 that is configured so as to extend toward the bicipital groove when the implant 2200 is implanted in the humerus of a patient. In some embodiments, the proximal portion 2210 includes a proximal end 2212, a distal end 2214, a medial side 2216, a lateral side 2218, an anterior end 2220, and a posterior end 2222. In some embodiments, the proximal portion 2210 includes a humeral head support engagement point 2260 at the proximal end 2212. In some embodiments, the humeral head support engagement point 2260 is substantially cylindrical. In some embodiments, the implant 2200 includes a humeral head support 2270. In some embodiments, the humeral head support 2270 is configured to be mounted to the humeral head support engagement point 2260 of the proximal portion 2210.

Figure 23:
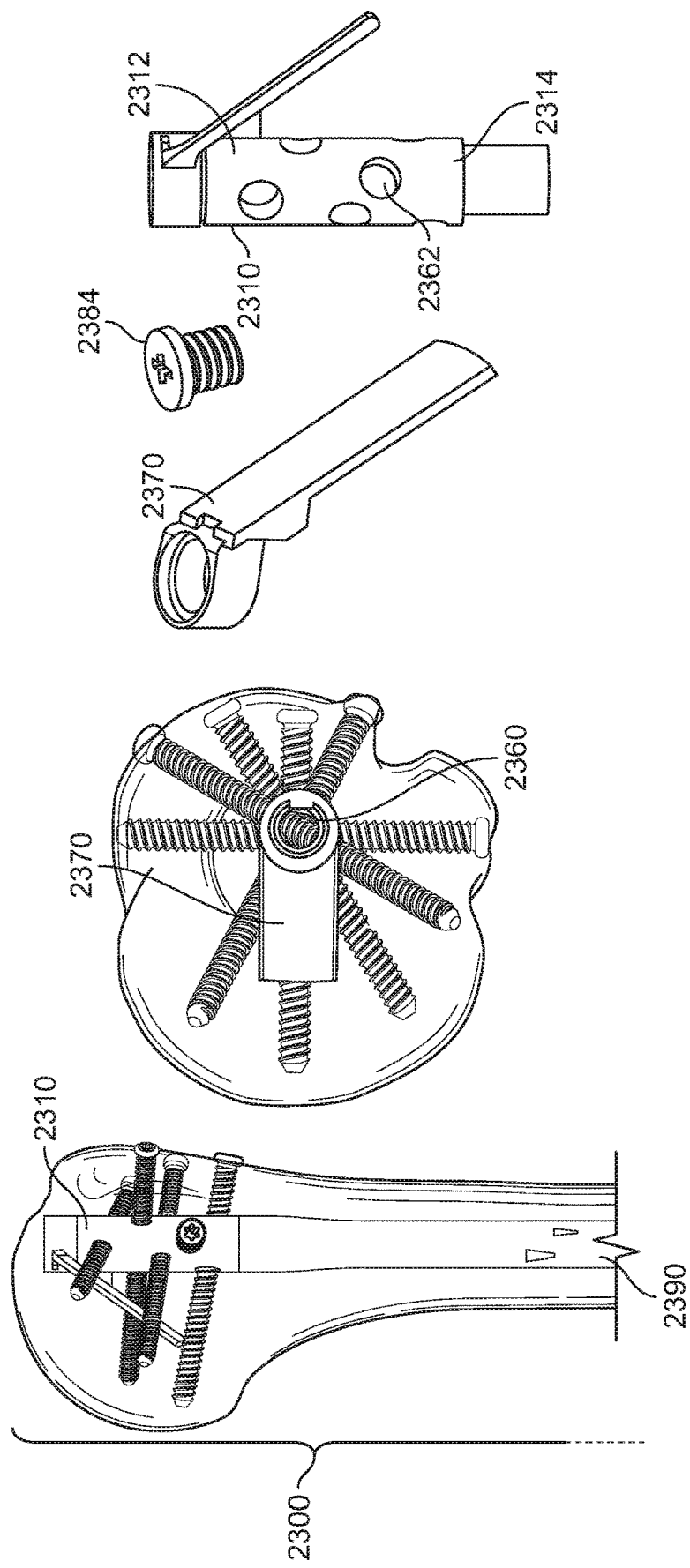
FIG. 23 shows a twelfth embodiment of a platform fracture fixation implant including a twelfth embodiment of a proximal portion of a platform fracture fixation implant and a humeral head support.

FIG. 23 illustrates various views of a twelfth exemplary embodiment of a platform fracture fixation implant 2300. In some embodiments, the platform fracture fixation implant 2300 includes a proximal portion 2310 and a distal portion 2390. In some embodiments, the proximal portion 2310 includes at least one anchoring point 2362 (e.g., a threaded hole) configured to receive screws or other anchoring elements, thereby to anchor portions of the humerus to the asymmetric proximal portion 2310. In some embodiments, the proximal portion 2310 includes a proximal end 2312 and a distal end 2314. In some embodiments, the proximal portion 2310 includes a humeral head support engagement point 2360 at the proximal end 2312. In some embodiments, the humeral head support engagement point 2360 is substantially cylindrical. In some embodiments, the implant 2300 includes a humeral head support 2370. In some embodiments, the humeral head support 2370 is configured to be mounted to the humeral head support engagement point 2360 of the proximal portion 2310. In some embodiments, the humeral head support engagement point 2360 includes a cylindrical portion with internal threading, and the implant 2300 includes a screw 2384 configured to mount the humeral head support 2370 to the humeral head support engagement point 2360.

In some embodiments, the various modular proximal and distal portions of platform fracture fixation implants described above may be manufactured from various different biocompatible materials, including, but not limited to, cobalt-chrome, stainless steel, titanium, titanium alloys, carbon fiber reinforced polymers, ceramic, poly(methyl methacrylate) ("PMMA") bone cement, pyrocarbon, bone graft, and/or any other suitable biocompatible material. In some embodiments, the various modular proximal and distal portions of platform fracture fixation implants described above may be fabricated by traditional computer added manufacturing processes, by using additive manufacturing or similar processes, or by any other suitable manufacturing process. In some embodiments, the various modular proximal and distal portions of platform fracture fixation implants described above may be surface coated or treated with various processes to encourage fixation to the soft tissue, muscle, and/or bone. In some embodiments, the various modular proximal and distal portions of platform fracture fixation implants described above may be porous over some or all of their surfaces so as to encourage bone ingrowth therein, and thereby encourage fixation to the bone.

While a number of embodiments of the present invention have been described, it is understood that these embodiments are illustrative only, and not restrictive, and that many modifications may become apparent to those of ordinary skill in the art. For example, all dimensions discussed herein are provided as examples only, and are intended to be illustrative and not restrictive. Further, any desired number and shape of screw hole(s), suture hole (s), etc. may be utilized (and may be placed in any desired location(s) on the prosthesis). Further still, while the term "fin" has been used throughout this application and may be thought to imply a separate, stand-alone feature, it is to be understood that the invention may, of course, utilize one or more surfaces of an essentially continuous structure in addition to (or in place of) a "fin".

What is claimed is:

1. A proximal portion of an implant for repairing a multipart fracture of a proximal end of a humerus of a human, the proximal portion comprising:
an asymmetric body having a proximal end, a distal end opposite the proximal end, a medial side, a lateral side opposite the medial side, an anterior edge, a posterior edge opposite the anterior edge, and a medial surface extending along at least a portion of the medial side, the medial surface having a proximal end and a distal end;
wherein the distal end is configured to be coupled to a proximal end of an intramedullary nail, and
wherein the asymmetric body is sized and shaped to be implanted so as to be surrounded by bone within a proximal volume of a humerus of a human;
a humeral head support, wherein the humeral head support comprises:
a base portion joined to the asymmetric body, and
a support portion extending from the base portion,
wherein the support portion extends from the base portion in a direction such that the support portion is configured to extend from the base portion diagonally in a medial and distal direction when the base portion is attached to the proximal end of the implant, and
wherein the support portion is positioned with respect to the base portion so as to be positioned between the humeral head of the humerus and a lesser tuberosity of the humerus so as to support the humeral head of the humerus during a repair of a four-part fracture of the humerus; and
at least one anchoring point formed in the asymmetric body, the at least one anchoring point configured to engage an anchoring device to thereby anchor the proximal portion to a portion of the humerus.

2. The proximal portion of claim 1, further comprising an engagement mechanism positioned at the distal end of the asymmetric body and configured to engage the proximal end of the intramedullary nail.

3. The proximal portion of claim 2, wherein the engagement mechanism is a taper.

4. The proximal portion of claim 1, wherein the proximal portion is integrally formed with the intramedullary nail.

5. The proximal portion of claim 1, wherein the protrusion includes a fin.

6. The proximal portion of claim 1, wherein the at least one anchoring point includes at least one threaded hole configured to receive at least one screw.

7. The proximal portion of claim 1, wherein at least a portion of an outer surface of the proximal portion is porous.

8. A kit for repairing a multipart fracture of a proximal end of a humerus of a human, the kit comprising:
a plurality of proximal portions, each of the plurality of proximal portions including:
an asymmetric body having a proximal end, a distal end opposite the proximal end, a medial side, a lateral side opposite the medial side, an anterior edge, a posterior edge opposite the anterior edge, and a medial surface extending along at least a portion of the medial side, the medial surface having a proximal end and a distal end;
a humeral head support, wherein the humeral head support comprises:
a base portion joined to the asymmetric body, and
a support portion extending from the base portion,
wherein the support portion extends from the base portion in a direction such that the support portion is configured to extend from the base portion diagonally in a medial and distal direction when the base portion is attached to the proximal end of the implant, and wherein the support portion is positioned with respect to the base portion so as to be positioned between the humeral head of the humerus and a lesser tuberosity of the humerus so as to support the humeral head of the humerus during a repair of a four-part fracture of the humerus;
at least one anchoring point formed in the asymmetric body, the at least one anchoring point configured to engage an anchoring device to thereby anchor the proximal portion to a portion of the humerus; and
an engagement mechanism positioned at the distal end of the asymmetric body and configured to engage a distal portion of the implant,
wherein each of the proximal portions within the kit is differently sized from all others of the proximal portions within the kit; and
a plurality of distal portions, each of the distal portions having a distal end configured for placement within a medullary cavity of the humerus and a proximal end configured for engagement with the engagement mechanism of a selected one of the plurality of proximal portions, wherein each of the plurality of distal portions within the kit is differently sized from all others of the proximal portions within the kit.

9. The kit of claim 8, wherein each of the plurality of proximal portions has a different size in a proximal-distal direction.

10. The kit of claim 8, wherein each of the plurality of proximal portions has a different size in an anterior-posterior direction.

11. The kit of claim 8, wherein each of the plurality of distal portions has a different length or a different diameter from all of the other distal portions within the kit.

12. The kit of claim 8, wherein the engagement mechanism of the plurality of proximal portions includes a taper.

13. The kit of claim 8, the at least one anchoring point of each of the proximal portions includes at least one threaded hole configured to receive at least one screw.

* * * * *